United States Patent [19]

Capuano

[11] Patent Number: 5,654,201
[45] Date of Patent: Aug. 5, 1997

[54] CHLORINE QUALITY MONITORING METHOD

[75] Inventor: Italo A. Capuano, Orange, Conn.

[73] Assignee: Olin Corporation, Cheshire, Conn.

[21] Appl. No.: 524,494

[22] Filed: Sep. 7, 1995

Related U.S. Application Data

[62] Division of Ser. No. 357,956, Dec. 16, 1994, Pat. No. 5,489,535.
[51] Int. Cl.⁶ .................................................... G01N 21/72
[52] U.S. Cl. .................... 436/124; 436/125; 436/55; 436/101; 422/80; 422/108
[58] Field of Search ............................. 422/80, 70, 108; 436/124–125, 146, 164, 55, 101

[56] References Cited

U.S. PATENT DOCUMENTS 4,778,764  10/1988  Fine ........................................ 436/124

*Primary Examiner*—Lyle A. Alexander
*Attorney, Agent, or Firm*—Dale Lynn Carlson; Wiggin & Dana

[57] ABSTRACT

An apparatus and method for monitoring the product quality of chlorine in which a sample stream of chlorine is taken from a chlorine stream and a portion of the sample stream is passed to one of three different analyzers for detection of various contaminants. A common data acquisition network receives data from each analyzer for integration and output. The analyzers include a bromine in chlorine analyzer, a non-condensable gas in chlorine analyzer, and a halocarbon in chlorine analyzer.

9 Claims, 13 Drawing Sheets

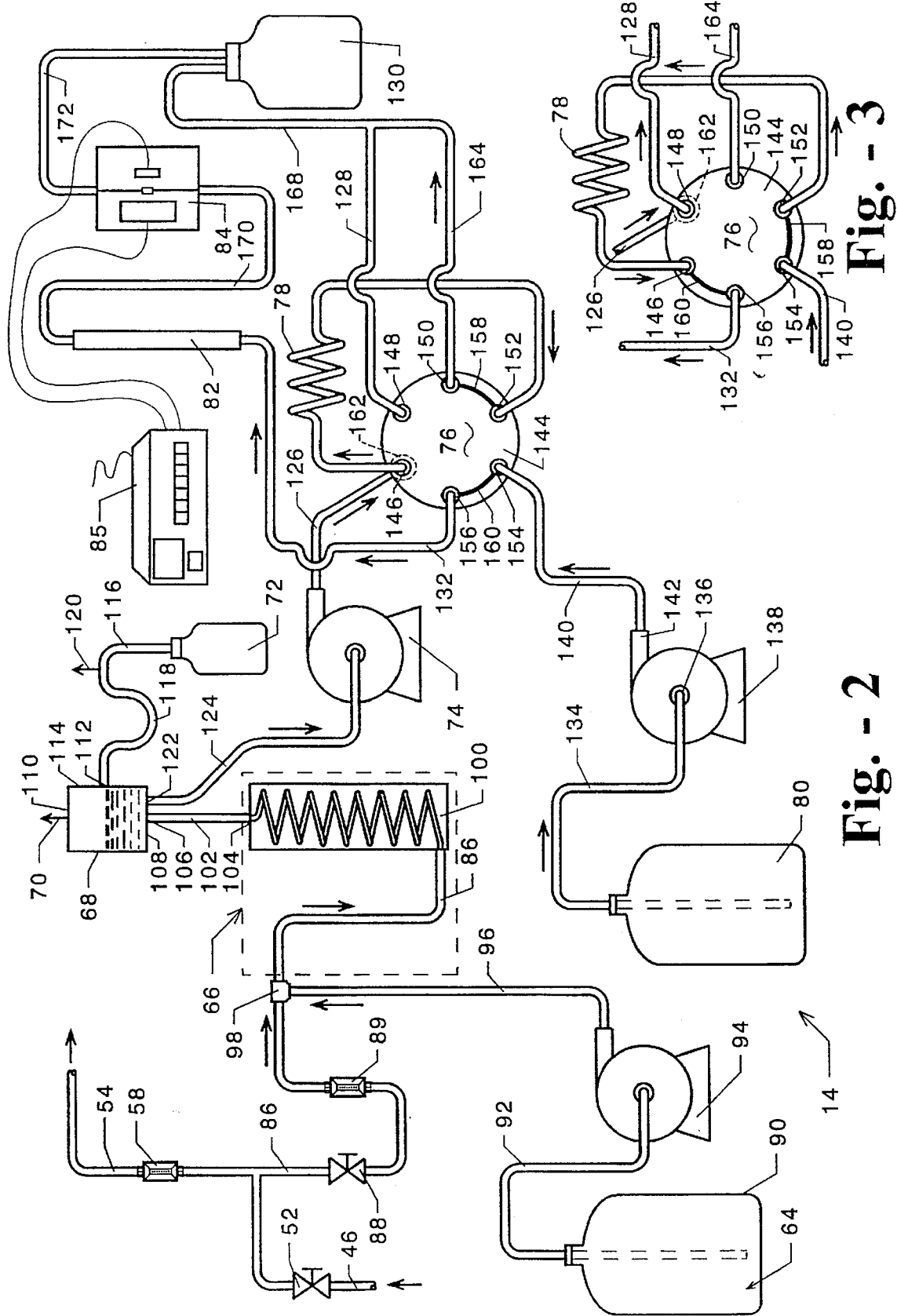

CHLORINE QUALITY MONITORING METHOD

This application is a division of application Ser. No. 08/357,956 filed Dec. 16, 1994 now U.S. Pat. No. 5,489,535.

BACKGROUND OF THE INVENTION

1. Field of the Invention

This invention relates generally to the monitoring of the product quality of chlorine. More particularly, this invention relates to a system and method for monitoring chlorine for the presence of various contaminants.

2. Background

The demand for purer chlorine products is generally increasing. Industrial chlorine users need to produce higher quality products derived from chlorine in order to meet increasingly stringent safety and environmental standards, as well as to improve manufacturing operations. For example, contaminants in chlorine such as non-condensable gases including oxygen, nitrogen and carbon dioxide are undesirable because they generate unwanted chemical waste which is costly to dispose of. These contaminants, which may remain in the excess chlorine from a chemical process, tend to deplete the scrubber through which the excess chlorine is passed for disposal, as well as form other compounds which must be disposed of. Bromine in chlorine contaminates the products made from chlorine, and decreases the reactivity of intermediates made from chlorine, thereby effecting the manufacture of the final product.

Additionally, public chlorine users such as municipalities need purer chlorine for water treatment to reduce the costs involved in the removal of carcinogenic materials such as halomethanes. Potable waters, which are normally disinfected with chlorine, must meet imposed standards on contaminants such as chloroform and carbon tetrachloride.

Due to the demand for purer chlorine by its users, chlorine manufactures are being increasingly compelled to monitor the various contaminants in chlorine during the manufacturing process to ensure that the chlorine being produced meets the demand for purity and to be able to take rapid corrective measures to reduce and/or eliminate the contaminants when they begin to appear. Particular contaminants which may be present in the produced chlorine and which are desired to be eliminated, or at least greatly reduced, include bromine, non-condensable gases such as oxygen, nitrogen and carbon dioxide, and halocarbons, including methylene chloride, chloroform and carbon tetrachloride. In order to monitor the contaminants and have the ability to take corrective action, it is necessary that a suitable system and method be available which will accurately detect and measure such contaminants and which can be used on-line at the production site and take samples directly from the process stream.

SUMMARY OF THE INVENTION

In view of the above, it is an object of the present invention to provide an improved system and method for measuring contaminants in chlorine.

A more specific object of the present invention is the provision of a system and method for measuring contaminants in chlorine which is easy to use and which can measure a plurality of different contaminants.

Yet another object of the present invention is the provision of a system and method for measuring contaminants in chlorine which can be used on line.

Still another object of the present invention is the provision of a system and method for monitoring contaminants in chlorine which can be used continuously.

A further object of the present invention is the provision of a method and analyzer which will detect and measure the presence of bromine in chlorine.

Yet still a further object of the present invention is the provision of a method and analyzer which will detect and measure the presence of non-condensable gases in chlorine.

Yet still another object of the present invention is the provision of a method and analyzer which will detect and measure the presence of halocarbons in chlorine.

These and other objects and advantages of the present invention may be achieved through the provision of a method for monitoring the product quality of chlorine which comprises taking a sample stream of chlorine from a stream of chlorine, passing a different portion of said sample stream to each of a plurality of analyzers, detecting the presence of bromine in the sample stream of chlorine by a first one of said analyzers, detecting the presence of non-condensable gases in the sample stream of chlorine by a second one of said analyzers, detecting the presence of halocarbons in the sample stream of chlorine by a third one of said analyzers, and passing the data regarding the presence of the detected material by each of the analyzers to a common data acquisition network for integration and output of the data.

An apparatus for monitoring the product quality of chlorine in accordance with the present invention may comprise a line for taking a sample stream of chlorine from a chlorine stream and a plurality of analyzers. Lines may be provided for taking a plurality of portions of the sample stream and passing a different portion of said sample stream to each of said analyzers, the first of said analyzers being a bromine in chlorine analyzer, a second of said analyzers being a non-condensable gas in chlorine analyzer, and a third of said analyzers being a halocarbon in chlorine analyzer. A data acquisition network common to all of the analyzers may be provided for receiving data from each analyzer and integrating and outputting the data.

According to another feature of the invention, a method of detecting the presence of bromine in a sample of chlorine may comprise reacting a stream of the chlorine sample with a reagent to form bromide ions, chloride ions and gas in an aqueous mixture, separating the gas from the aqueous mixture containing the bromide ions and chloride ions, injecting a sample of the aqueous mixture containing the bromide ions and chloride ions into a liquid carrier stream, separating said bromide ions and said chloride ions in said carrier stream, and passing said carrier stream with said separated ions through an ultraviolet detector and detecting the presence of the bromide ions in the sample passing therethrough.

An analyzer for detecting the presence of bromine in a sample of chlorine in accordance with the present invention may comprising a reaction zone for reacting a stream of the chlorine sample with a reagent to form bromide ions, chloride ions and gas in an aqueous mixture, a separator for separating the gas from the aqueous mixture containing the bromide ions and chloride ions, a liquid carrier stream, an injector for injecting a sample of the aqueous mixture containing the bromide ions and chloride ions into said liquid carrier stream, a chromatographic column for separating said bromide ions and said chloride ions in said carrier stream, and an ultraviolet detector for detecting the presence of the bromide ions when the carrier stream containing the separated bromide and chloride ions is passed therethrough.

A method of detecting the presence of non-condensable gases in a sample of chlorine according to the present invention may comprise injecting a sample of chlorine into a gaseous carrier stream, passing said carrier stream with said sample into a first chromatographic column to separate any non-condensable gases in said sample from the chlorine, passing said carrier stream with the non-condensable gases to a second chromatographic column while said chlorine remains in said first column, separating a first set of non-condensable gases from at least one other non-condensable gas in said second chromatographic column, temporarily storing said first set of gases in a third chromatographic column while said another non-condensable gas is passed to a detector for detection and measurement of that particular gas, passing said first set of non-condensable gases after separation to said detector upon completion of the passing of said another non-condensable gas, and backflushing said chlorine from said first chromatographic column with a stream of carrier gas to remove the chlorine from the column and out of the system.

Further, in accordance with the present invention, an analyzer for detecting the presence of non-condensable gases in a sample of chlorine may comprise an injector for injecting a sample of chlorine into a gaseous carrier stream, a first chromatographic column to separate any non-condensable gases in said sample from the chlorine, a second chromatographic column for separating a first set of non-condensable gases from at least one other non-condensable gas, a storage column for temporarily storing and separating said first set of gases from each other, a detector for detecting the presence of the non-condensable gases passing therethrough, a valve arrangement for passing said another non-condensable gas to said detector while said first set remains in said storage column and for passing said first set of non-condensable gases to said detector upon completion of the passing of said another non-condensable gas and while said chlorine remains in said first chromatographic column, and means for backflushing said chlorine from said first chromatographic column with a stream of carrier gas to remove the chlorine from the column and out of the system.

A method of detecting the presence of halocarbons in a sample of chlorine according to the present invention may comprise injecting a sample of chlorine into a first carrier stream, passing said first stream containing said sample through a chromatographic column to separate any halocarbons from each other and from the chlorine, diverting the chlorine from the system after it exits the column, passing a first group of halocarbons exiting from the column to a flame ionization detector for detection of each component of said first group, and passing a second carrier stream through said chromatographic column after said first group of halocarbons have exited therefrom in a direction opposite to the flow of the said first stream to carry any halocarbons remaining in the column from the column to the detector for measurement as a group.

An analyzer for detecting the presence of halocarbons in a sample of chlorine according to the present invention may comprise an injector for injecting a sample of chlorine into a first carrier stream, a chromatographic column to separate various halocarbons from each other and from the chlorine, a flame ionization detector for detection of said halocarbons, a diverter for diverting the chlorine after it exits said column away from the detector, and a valve arrangement for directing a first stream of carrier fluid to carry a first group of separated halocarbons from said chromatographic column to said detector and for directing a second carrier stream through said chromatographic column in a backward direction after said first group of halocarbons have exited therefrom and carry any halocarbons remaining in the column from the column to the detector for measurement as a group.

BRIEF DESCRIPTION OF THE DRAWINGS

The objects and advantages of the present invention will become more apparent by reference to the following detailed description and to the accompanying drawings in which:

FIG. 2 is a schematic diagram of the portion of the system of FIG. 1 comprising the analyzer for the detection and measurement of bromine in chlorine;

FIG. 3 is a schematic diagram of the control valve shown in FIG. 2, with the valve schematically shown in its injecting position;

DETAILED DESCRIPTION

Figure 1:
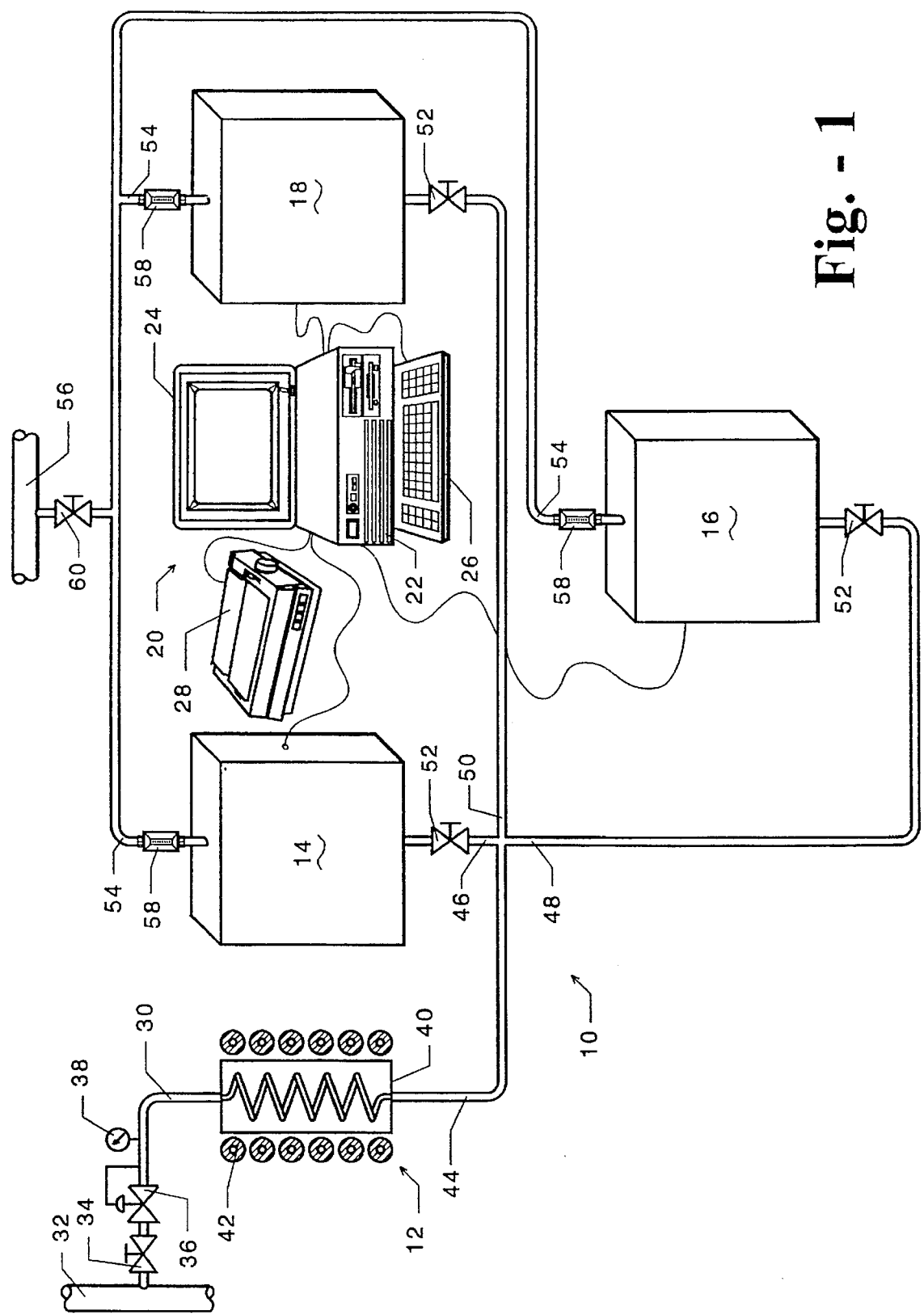
FIG. 1 is a schematic drawing of the overall monitoring system of the present invention.

Referring to the drawings, and particularly FIG. 1, there is shown a schematic diagram of a system 10 for monitoring the quality of chlorine which incorporates the principals of the present invention. In general, the preferred system comprises a vaporizer 12 to convert the incoming liquid chlorine into gaseous chlorine, a bromine in chlorine analyzer 14, a non-condensable gas in chlorine analyzer 16, a halocarbons in chlorine analyzer 18, and a data acquisition network 20. The data acquisition network 20 may include a computer 22, a monitor 24, a keyboard 26 and an output device such as a printer 28.

More specifically, a chlorine sample input line 30 is connected to a line 32 of the process stream containing the chlorine. The connection of the input line 30 to the process stream line 32 is preferable made at a point downstream of the process compressor which converts the chlorine into its liquid form. Accordingly, the sample of the chlorine taken from the process stream line 32 is preferably in liquid form. By taking the sample after the process compressor and in the liquid state, it is ensured that the sample will contain all the contaminants as in the chlorine product. Such process stream line 32 may be a feed line to a chlorine storage vessel or to a transport vessel such as a rail tank car or the like.

The input line 30 contains a cut-off valve 34 adjacent the connection to the process stream line 32. This valve 34 may be any suitable type of shut off valve such as a needle valve. A pressure regulator 36 is provided in the input line 30, downstream of the shut-off valve 34 to regulate the pressure of the incoming liquid chlorine. A pressure gauge 38 is provided in the input line 30, down stream of the pressure regulator 36 to provide an indication of the pressure of the incoming chlorine.

The input line 30 is connected at its downstream end to the vaporizer 12 which serves to change the liquid chlorine into gaseous chlorine. The vaporizer 12 may be a heat exchanger 40 which is heated by electrical power such as electrical heating coils 42 or may utilize steam as the heat source. The heat exchanger 40 should be maintained at a temperature sufficient to ensure that the chlorine exiting therefrom is in its gaseous form and there is complete vaporization and not fractionation of the volatiles. By way of example, the heat exchanger 40 may be maintained at a temperature between 100° C. and 150° C.

The chlorine sample stream exits the vaporizer 12 in gaseous form into a gaseous chlorine line 44 which splits into three input lines, a bromine analyzer input line 46, a halocarbon analyzer input line 48 and a non-condensable gas analyzer input line 50. Each of the input lines 46, 48 and 50 have a shut-off valve 52 positioned therein to shut off the flow of gaseous chlorine to its respective analyzer when necessary, as, for example, in the event that maintenance of an individual analyzer is needed. Such valves 52 may be any suitable type of shut-off valve resistant to chlorine and which can be manually actuated to shut off the flow. The valves 52 may preferable be needle valves.

Excess chlorine from each of the analyzers is discharged through a sample return line 54 back into a process stream line 56. As the chlorine being returned is in gaseous form, the excess chlorine should be returned to the process stream at a point at which the chlorine therein is also is gaseous form. Flow meters 58 are positioned in the return conduit 54, one associated with each of the analyzers 14, 16 and 18 to provide an indication of the flow of the excess chlorine from its respective analyzer. A shut-off valve 60 is positioned in the return conduit 54 immediately before its connection to the process stream line 56 to provide for isolation of the system 10 from the process stream when necessary.

The data acquisition network 20 receives input from the individual controllers of each of the analyzers 14, 16 and 18, and converts the input into suitable data for recording and output.

FIG. 2 shows a schematic diagram of the bromine in chlorine analyzer 14. The analyzer 14 includes generally a source 64 of an aqueous solution of hydrazine which is caused to react with the chlorine sample in a reaction area 66 to form chloride ions, bromide ions from any bromine present in the sample and nitrogen gas. The reacted gas-liquid mixture flows to a separator 68 in which the nitrogen escapes through a vent 70 while a portion of the liquid is discarded into a waste receptacle 72. A pump 74 meters a portion of the remaining liquid to a sampling valve 76. The sampling valve 76 serves to cyclically connect the liquid from the pump 74 to a sample loop 78. A carrier fluid from a source 80 is connected for flow to the sampling valve 76. The sampling valve 76 cyclically connects the carrier fluid with the sample loop 78 for carrying the sample from the sample loop 78 through a chromatographic column 82 and then to an ultraviolet detector 84. A microprocessor 85 converts the signals from the detector 84 into an output indicative of the amount of bromine present in the sample.

More specifically, still referring to FIG. 2, the bromine in chlorine analyzer 14 receives the gaseous chlorine from the vaporizer 12 through line 46. A portion the chlorine from line 46 is passed to the reaction area 66 by means of a conduit 86. The excess chlorine exits the bromine in chlorine analyzer 14 through the sample return line 54 and is returned to the chlorine process stream. A flow control valve 88 is provided in the conduit 86 to control the flow of the chlorine into the reaction area 66. A flow meter 89 is also positioned in the conduit 86 to provide an indication of the flow rate of the chlorine to the reaction area 66.

The source 64 of the aqueous solution of hydrazine may be in a suitable storage vessel such as a tank 90 which contains a supply of a hydrazine aqueous solution ($N_2H_4$) to provide a source of hydrazine to react with the chlorine. A conduit 92 connects the contents of the storage vessel 90 with a pump 94 which serves to meter a small flow of the hydrazine solution into a line 96 which connects with the conduit 86 containing the chlorine sample at a junction 98 located upstream of the flow meter 89. When the hydrazine enters the conduit 86, it begins to immediately react with the chlorine to form chloride ions, bromide ions from any possible bromine present in the chlorine sample, and nitrogen gas according to the formula:

$$N_2H_4 + Cl_2 + Br_2 \xrightarrow{H_2O} N_2\uparrow + 2H^+Cl^- + 2H^+Br^-$$

This reaction continues to progress in the conduit 86 and into a reactor 100. The reactor 100 my be simply a coiled tubing of a length sufficient to ensure that the reaction is completed before the liquid-gas mixture leaves the reactor 100 and enters the separator 68. A reaction output line 102 connects an outlet 104 of the reactor 100 with an inlet 106 in the bottom 108 of the separator 68 to provide for the passage of the reacted gas-liquid mixture to the separator 68. The separator 68 may be any suitable type of closed vessel with the vent 70 preferable in its top surface 110 and an overflow outlet 112 in its side wall 114 at an appropriate height from the bottom 108 of the separator 68. The overflow outlet 112 is Connected to a waste line 116 having a U-shaped trap 118 and a vent 120 therein. The waste line 116 is connected to the waste receptacle 72 which serves to collect the discarded liquid from the separator 68. The trap 118 in the waste line 116 serves to prevent any gas from passing from the separator 68 to the waste receptacle 72.

The separator 68 thus serves to permit the nitrogen gas to escape through the vent 70 while a portion of the liquid is discarded to the waste receptacle 72. A portion of the remaining liquid passes through a sample outlet 122 in the bottom 108 of the separator 68 to which one end of a sample feed conduit 124 is connected. The other end of the sample feed conduit 124 is connected to the metering pump 74. A sample infeed conduit 126 connects the outlet of the pump to the sampling valve 76.

The sampling valve 76 serves to connect the flow of the reacted liquid mixture from the metering pump 74 cyclically to either the sample loop 78 or directly to a waste line 128 leading to a waste receptacle 130. Additionally, the sampling valve 76 serves to connect the source 80 of the carrier fluid cyclically to either the sample loop 78 for carrying a sample in the loop 78 to the chromatographic column 82, or to a line 132 going directly to the chromatographic column 82.

A carrier fluid supply line 134 is provided to connect the source 80 of a carrier fluid to an inlet 136 of a metering pump 138. A carrier fluid feed line 140 has one end connected to an outlet 142 of the metering pump 138 and its other end connected to the sampling valve 76.

The carrier fluid is preferably an aqueous solution of sodium chloride, but other salts such as potassium chloride may be used.

The sampling valve 76 is preferably a standard six port sample injection valve. Valves of this type may generally include a stator 144 having six ports 146, 148, 150, 152, 154 and 156 therein as indicated by the small circles shown in FIG. 2. The two heavy arcs 158 and 160, as shown in the drawing, represent the connecting passages in the rotor seal. The dotted circle represents the sample inlet port 162 in the rotor and rotor seal (not shown) of the valve 76 and which is movable therewith. The sampling valve 76 may be pneumatically actuated and controlled by using a 4-way solenoid-actuated valve (not shown) which is electrically connected by suitable connections to the microprocessor 85. An example of a suitable sampling valve is the Rheodyne Model 7126 Automatic Sampling Injector manufactured by Rheodyne Incorporated, Cotati, Calif. Other suitable valves or valve arrangements may be used so long as any such valves or valve arrangements will function to provide for the loading a sample loop with a sample, flushing of the chromatographic column and injecting the sample into the chromatographic column by the carrier liquid as described below.

As shown in FIG. 2, one end of the sample loop 78 is connected to the port 146 of the sampling valve 76, and the other end to the port 152. The carrier fluid infeed line 140 is connected to the port 154. The waste line 128 is connected to the port 148 and a second waste line 164 is connected to the port 150o The waste lines 128 and 164 join together to form a common waste line 168 which is connected to a waste receptacle 130. The line 132 to the chromatographic column 82 is connected to the port 156 of the sampling valve 76. The chromatographic column is connected by a line 170 to the ultraviolet detector 84, the outlet of which is connected by a line 172 to the waste receptacle 130.

In the deactive position of the sampling valve 76 in which the sample flows through the sample loop 78, the ports of the valve are positioned as shown in FIG. 2. In this deactive position, the sample inlet port 162, to which the sample infeed conduit 126 is connected, communicates with the port 146 in stator of the sampling valve 76 to which one end of the sample loop 78 is attached. The connecting passage 158 in the valve 76 provides communication between the port 152 to which the other end of the sample loop 76 is connected and the port 150 to which the waste line 164 is connected. Accordingly, in the deactive position of the sampling valve 76, the liquid sample stream from the pump 74 flows into the valve 76 from the line 126 through the inlet port 162, exits the valve through the port 146, passes through the sample loop 78 and flows back into the valve 76 through port 152. The liquid sample stream then passes through passageway 158 in the valve 76, out of the valve 76 through port 150, and into the waste lines 164 and 168 to the waste receptacle 130.

Additionally, when the sampling valve 76 in its deactive position, the carrier fluid passes from the carrier feed line 140 into port 154 of the valve 76, and then through the passageway 160 in the valve rotor and out through port 156 of the valve 76 into the line 132 which is connected to the chromatographic column 82. Thus, in the deactive position of the valve 76, the carrier fluid passes through the valve 76 directly to the chromatographic column 82 and then through the ultraviolet detector 84 to the waste receptacle 130. This serves to flush the chromatographic column 82 and detector 84 prior to the next analysis.

The chromatographic column 82 may be any commercially available standard high performance ion chromatographic column which will separate the bromide ions from the excess hydrazine reagent and from the large concentration of chloride ions. One suitable chromatographic column is the IONPAC® AS10 Analytical Column manufactured by DIONEX Corporation of Sunnyvale, Calif.

The ultraviolet detector 84 may be any standard commercially available ultraviolet detector which is capable of use with liquids. An example of one such detector is the ISCO® Model No. 229 UV/Visible detector by Isco, Inc. The detector is set to operate on a wavelength of 210 nanometers which is the frequency at which the bromide ion absorbs substantially more light than hydrazine and the chloride ion. The measurement of the bromide ion as a function of the bromine possibly present in the chlorine sample taken from the process stream is carried out through calculations by the microprocessor 85 and is transmitted to the data acquisition network 20.

The timing sequence for the analytical cycle may be programmed into the microprocessor 85. At the start of the cycle, the microprocessor 85 sends a command to actuate the sampling valve 76 into its activated position. FIG. 3 shows the relationship of the ports and passages of the sampling valve 76 when the valve 76 has been actuated into its activated position. As shown, the rotor and rotor seal of the valve 76 has been moved, moving the passages 158 and 160 relative to the stator so that passage 158 interconnects the ports 152 and 154. Passageway 160 interconnects the ports 146 and 156. The sample inlet port 162 is also moved so that in the activated position, it connects with the port 148.

With this arrangement, the carrier fluid passes from the line 140 into the port 154 in the valve 76 through passage 158, out through the port 152 and through the sample loop 78. The carrier fluid carriers the sample in the sample loop 78 into the valve 76 through the port 146, through the passage 160 and out through the port 156 into the line 132 to the chromatographic column 82. The chlorine sample flow from the sample input line 126 enters the inlet port 162 of the valve 76 and flows out of the valve 76 through port 148 and into the waste lines 128 and 168 to the waste receptacle 130.

As the sample from the sample loop 78 being carried by the carrier fluid passes through the chromatographic column 82, the bromide ions are separated from the hydrazine and chloride ions. The chloride ions and hydrazine elution occurs first, followed by the elution of the bromide ions. The chloride ions and hydrazine exit the column 82 first, followed by the bromide ions, and pass to the detector 84 in this order. The detector 84 passes an ultraviolet light through the sample passing through the chamber of the detector. The ultraviolet light is absorbed by the ions, causing the excitation thereof, and generating a current. This current is proportional to the amount of ions present. This current flow is passed to the microprocessor 85 which converts this current signal to a reading indicative of the bromine present in the sample. At a given point in time after the sample has been carried from the sample loop 78 by the carrier stream to the chromatographic column, the valve 76 is actuated in response to a command from the microprocessor 85 back into its deactive position permitting sample from the incoming sample feed line 126 to flow through the sample loop 78 ready for the next analysis.

While not specifically shown in the drawings, the reaction zone 66, the carrier fluid source 80, the sampling valve 76, the sample loop 78, chromatographic column 82 and detector 84, as well as the associated piping are all temperature controlled. This ensures that there will be no variations in temperature after the system has been calibrated which would effect their accuracy of the readings from one analysis to another.

The initial calibration may be achieved by passing a calibration chlorine sample containing a known amount of bromine into the reaction zone. The sampling valve is activated with the detector 84 set at the wave length at which the bromide ions are detected and measured. Given the flow rates of the chlorine sample, the hydrazine, and the carrier fluid, which will remain constant from one analytical cycle to another, the time is noted for the carrier fluid to carry the sample from the sample loop 78 to the chromatographic column 82 and for the elution of the bromide ions and passage thereof through the detector. This information may be used to set the timing of the analytical cycle. The reading of the microprocessor calculated from the detector signal when the calibration sample is passing therethrough is adjusted to reflect the true amount of bromine in the sample. This provides a set point for the other concentrations.

By way of example, the analyzer 14 may provide for an incoming flow rate of the chlorine sample of 100 milliliters per minute (ml/min.) The hydrazine may be in the form of a 2.5% aqueous solution and have a flow rate to the reaction zone of 2 ml/min. The temperature of the reaction may be maintained at 25° C. The carrier fluid may be a 50 millimolar solution of potassium chloride (KCl) in water and have a flow rate of 1.5 ml/min. The chromatographic column as mentioned above may be a IONPAC® AS-10 which may be maintained at 40° C. The detector may be an ultraviolet detector set at 210 nanometers.

With this arrangement, the analysis cycle will be about 400 seconds. The sampling valve 76 is switched to its activated position at the start of the cycle at a time equal to zero seconds. The chloride ion and hydrazine reagent elution will occur at a point between about 80 seconds and 150 seconds into the cycle. The bromide ion elution will occur between about 200 and 350 seconds into the cycle. The chlorine sample will have been removed from the sample loop 76 at a time prior to the elution of any of the components so that the sampling valve 76 may be returned to its inactive position as early as 50 seconds into the cycle to feed a new stream of chlorine sample into the sample loop 78. The start of the next cycle should be delayed for at least 400 seconds (about 50 seconds after the elution of the bromide ion) so there will be a sufficient period of time after which all components of the sample will have passed through the detector for the carrier fluid to purge the chromatographic column and the detector before they receive the next sample.

Figure 4:
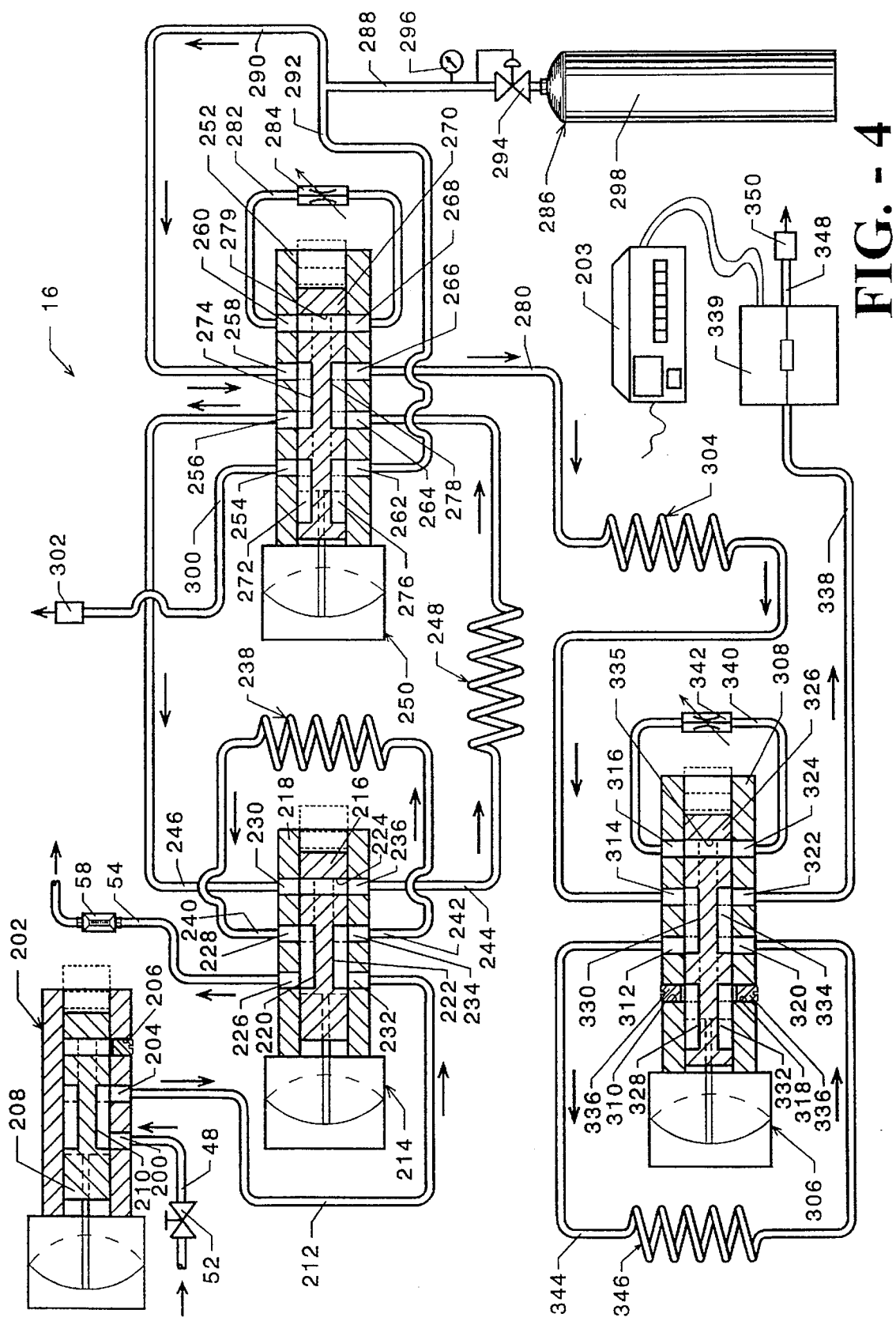
FIG. 4 is a schematic diagram of the portion of the system of FIG. 1 comprising the analyzer for the detection and measurement of non-condensable gases in chlorine, and showing the position of the valves and flow through the system while the system is inactive.

The non-condensable gases in chlorine analyzer is schematically shown in FIG. 4. This analyzer provides for the detection and analysis of non-condensable gases, usually oxygen, nitrogen and carbon dioxide, by an analytical chromatographic scheme.

In accordance with the arrangement shown in FIG. 4, the sample feed line 48 containing a flow of the gaseous chlorine from the vaporizer 12 is connected to one port 200 of a sample cut-off valve 202. This valve 202 may be any suitable type of electrically controlled, on-off valve and which can be controlled by a microprocessor 203. Preferably, the valve 202 is a modified six-port slider plate valve which is pneumatically actuated between a deactive position and an activated position. A solenoid valve (not shown), controlled by the microprocessor 203, may control the supply of pneumatic fluid such as instrument air to the valve 202 to cause the movement of the valve between its two positions.

The valve 202 is modified by eliminating or blocking the series of ports which are normally on one side of the valve (the top side as view in FIG. 4). Also, of the three ports 200, 204 and 206 on the other side, the port 206 is blocked as indicated. This, in effect, leaves two active ports 200 and 204.

A moveable slider plate 208 within the valve 202 has a groove or passage 210 therein which interconnects the two ports 200 and 204 when the valve 202 is in its deactive position as shown by the solid lines in the drawing. When the valve 202 is actuated into its activated position, the slider plate 208 is moved into the off-position as shown by the dotted lines in the drawing, wherein the passage 210 is out of alignment with the port 200 and there is no communication, and thus, no flow between ports 200 and 204.

One end of a sample in-feed line 212 is connected to the port 204 of the valve 202. The other end of the sample infeed line 212 is connected to a sampling valve 214.

The sampling valve 214 may be a standard 8-port commercially available slider plate valve which is pneumatically actuated between a deactive or sample loading position and an activated or sample injecting position. A solenoid valve (not shown), controlled by the microprocessor 203, may control the supply of the pneumatic fluid such as instrument air to the valve 214 to cause the movement of the valve between its two positions.

The sampling valve 214 may include a slider plate 216 movable in a body 218 between the two positions of the valve. The slider plate 216 may include a first groove or passage 220 which extends axially in the top surface of the slider plate 216 as viewed in FIG. 4. A second groove or passage 222 may extend axially in the bottom surface of the slider plate 216. A through-bore or passage 224 extends between the top and bottom surfaces of the slider plate 216.

The body 218 of the sampling valve 214 may include six ports 226, 228, 230, 232, 234 and 236, with the ports 226, 228 and 230 being positioned in the top surface of the body and the ports 232, 234 and 236 being positioned in the bottom surface of the body 218 when the valve is orientated as shown in FIG. 4.

When the sampling valve 214 is in its deactive or loading position, the slider plate 216 is positioned as shown by the solid lines in FIG. 4. In the deactive or loading position, the passage 220 connects the ports 226 and 228, while passage 222 connects the ports 232 and 234. The through bore or passage 224 in the slider plate 216 connects the ports 230 and 236. When the valve 214 is actuated into its activated, or injecting position, the slider plate 216 is moved to the right as viewed in FIG. 4, assuming the position indicated by the dotted lines. In the activated or injecting position, the passage 220 connects the ports 228 and 230 and passageway 222 connects the ports 234 and 236. The ports 226 and 232 are blocked and the through-bore or passage 224 is not active.

The sample infeed line 212 from the sample cut-off valve 202 is connected to port 232 of the sampling valve 214. The sample return line 54 with the flow meter 58 therein is connected to port 226. A sample loop 238 has one end 240 connected to port 228 and its other end 242 connected to port 234. A sample outlet line 244 is connected to port 236 and a carrier stream line 246 is connected to port 230.

The sample outlet line 244 from the sampling valve 214 includes a first chromatographic column 248 therein. This column 248 serves to separate the oxygen and nitrogen as bulk from the chlorine and carbon dioxide. One suitable type of chromatographic column may be an oil impregnated diatomaceous earth material packed in a tubular column. By way of example, the preferred column is a 10 foot length of ¼ inch tubing packed with Chromosorb® W material (a diatomaceous silica) which is impregnated with 15% by weight SF-96, a silicon oil. Chromosorb® is a trademark of Manville Products.

The sample outlet line 244 containing the first chromatographic column 248 is connected to a backflush valve 250. The backflush valve 250 may be a standard commercially available eight port slider plate valve which is pneumatically actuated between a deactive position and an activated position. An electrically operated solenoid valve (not shown) may be used to control the supply of pneumatic fluid such as instrument air to the valve 250 to cause the actuation of the backflush valve 250 between its two positions. The solenoid valve may in turn be controlled by the microprocessor 203.

In general, the backflush valve 250 includes a valve body 252 having eight ports 254, 256, 258, 260, 262, 264, 266 and 268 therein. A slider plate 270 is slidably mounted in the body 252 for movement between the deactivate and activated positions of the valve 250. The slider plate 270 includes two grooves or passages 272 and 274 in its upper surface (as viewed in FIG. 4) and two grooves or passages 276 and 278 in its bottom surface. A through-bore or passage 279 extends between the upper and lower surfaces of the slider plate 270 as shown.

In the deactive position of the backflush valve 250, in which the slider plate 270 is positioned in its retracted position as shown by the solid lines in FIG. 4, the passage 272 is aligned only with the port 254, thereby effectively blocking the port 254. The passage 274 connects the ports 256 and 258. The passage 276 is aligned only with the port 262, thereby effectively blocking the port 262. The passage 278 connects the ports 264 and 266 and the through-bore or passage 279 connects the ports 260 and 268.

In the activated position of the backflush valve 250, the slider plate 270 is extended to the right as viewed in FIG. 4 into the position indicated by the dotted lines. In this position, the passage 272. interconnects the ports 254 and 256 and passage 274 interconnects the ports 258 and 260. Also, in the activated position, the passage 276 interconnects the ports 262 and 264 and the passage 278 interconnects the ports 266 and 268. The through-bore or passage 279 is inactive in this position of the valve 250.

The sample outlet line 244 from the sampling valve 214 containing the first chromatographic column 248 is connected to the port 264 of the backflush valve 250. A sample feed line 280 is attached to the port 266. A loop 282, containing an adjustable flow restrictor 284 has one end connected to port 260 and its other end connected to the port 268.

A source 286 of a carrier gas may be connected to a carrier gas infeed line 288 which is split into a first carrier gas stream line 290 and a second carrier gas stream line 292. The carrier gas infeed line 288 may include a pressure regulator 294 to control the pressure of the incoming carrier gas, and a pressure gauge 296 to provide an indication of the pressure. The carrier gas may be any suitable type of gas which will not react with any components of the sample stream, does not contain any of the components for which the analysis is being conducted, and will not interfere with the detection of the components by the detector. Specifically, the carrier gas may be a suitable inert gas and is preferably highly purified helium gas which may be provided in a suitable storage tank 298.

The first carrier gas stream line 290 is connected to the port 258 of the backflush valve 250 and the second carrier gas stream line 292 is connected to the port 262. A waste chlorine discharge line 300 is connected to the port 254 of the backflush valve 250 for discharging waste chlorine to a suitable scrubber 302.

The sample feed line 280 from the backflush valve 250 includes a second chromatographic column 304 therein. This column 304 serves to separate the oxygen and nitrogen from the carbon dioxide. The column 304 may be in the form of coiled tubing packed with a polymer. In the preferred form, the column is a 10 foot length of coiled ¼ inch tubing packed with HayeSep® R powder, a polymeric powder. Such powders are commercially available from Alltech Associates, Inc. of Deerfield, Ill. HayeSep® is a trademark of Hayes Separation, Inc.

The end of the sample feed line 280 opposite the backflush valve 250 is connected to a storage valve 306. The storage valve 306 may be a standard, commercially available, eight port slider plate valve similar to the valve 250 and which is pneumatically actuated between a deactive position and an activated position. An electrically operated solenoid valve (not shown) may be used to control the supply of pneumatic fluid such as instrument air to the valve 306 to cause the actuation of the valve between its two positions. The solenoid valve is in turn controlled by the microprocessor 203.

In general, the storage valve 306 includes a valve body 308 having eight ports 310, 312, 314, 316, 318, 320, 322 and 324 therein. A slider plate 326 is slidable mounted in the body 308 for movement between the activated and inactive positions of the valve 306. The slider plate 326 includes two grooves or passages 328 and 330 in its upper surface (as viewed in FIG. 4) and two grooves or passages 332 and 334 in its bottom surface. A through-bore or passage 335 extends between the upper and lower surfaces of the slider plate 326 as shown.

In the deactive position of the valve 306, in which the slider plate 326 is positioned in its retracted position as shown by the solid lines in FIG. 4, the passage 328 is aligned only with the port 310. The passage 330 connects the ports 312 and 314. The passage 332 is aligned only with the port 318. The passage 334 connects the ports 320 and 322, and the through-bore or passage 335 connects the ports 316 and 324. The ports 310 and 318 may be permanently closed by plugs 336 or other suitable means so that they are rendered inactive in both positions of the storage valve 306. While an eight port valve is used in the preferred embodiment, other types of valves such as a six port slider plate valve may be used.

In the activated position of the storage valve 306, the slider plate 326 is extended to the right as viewed in FIG. 4 into the position indicated by the dotted lines. In this position, the passage 328 interconnects the ports 310 and 312 and the passage 330 interconnects the ports 314 and 316. Also, in the activated position, the passage 332 interconnects the ports 318 and 320 and the passage 334 interconnects the ports 322 and 324. The through-bore or passage 279 is inactive in this position of the valve 250. Additionally, as the ports 310 and 318 are plugged, the ports 312 and 320 are blocked in the activated position of the valve 306, thereby blocking off or isolating the molecular sieve column 346.

The sample feed line 280, connected at one end to the backflush valve 250 and containing the second chromatographic column 304, is attached at its other end to the port 314 of the storage valve 306. A carrier-sample flow line 338 leading to a detector 339 is attached to the port 322 of the storage valve 306. A loop 340, containing an adjustable flow restrictor 342, has one end connected to the port 316 of the storage valve 306 and its other end connected to the port 324. A storage loop 344 containing a third chromatographic column in the form of a molecular sieve column 346 has one end connected to port 312 of the storage valve 306 and its other end connected to port 320.

The molecular sieve column 346 functions to separate the oxygen and nitrogen which are temporarily stored in the loop 344 as will be explained below. The molecular sieve may be any suitable material capable of achieving the desired separation of the oxygen and nitrogen and preferably is a 5 Å (Angstrom) sieve contained in a 10 foot length of coiled ¼ inch tubing.

The carrier-sample flow line 338 from the port 322 of the storage valve 306 is connected to the discharge ionization detector 339 for supplying the sample to the detector for analysis. The sample passes from the detector to a waste line 348 which leads to a caustic scrubber 350 for disposal of the sample material.

The detector 339 is preferably a discharge ionization detector containing its own power control. Any suitable commercially available discharge ionization detector may be used. An example of one such detector is Model 24-600 sold by Gow-Mac Instrument Co. The detector 339 sends an electrical signal proportional to the level of a particular component of the sample stream being analyzed to the microprocessor 203 which converts the signal into a reading indicative of the level of that particular component. The microprocessor 203 sends the information about a particular component to the common data acquisition network 20 for processing.

In operation, the sample cut-off valve 202, the sampling valve 214, the backflush valve 250 and the storage valve 306 are maintained in their deactive positions until it is desired to begin an analysis. The operation of the analysis cycle is controlled by the microprocessor 203.

In the deactive positions of the valves 202, 214, 250 and 306, the chlorine sample in gaseous form from the vaporizer 12 flows into the sample cut-off valve 202 through port 200, flows through passage 210 and out of the cut-off valve 202 through the port 204 into the feed line 212 leading to the sampling valve 214.

The gaseous chlorine sample enters the sampling valve 214 from the feed line 212 through port 232, passes through passage 222 and exits the valve 214 through port 222 into the sample loop 238. From the sample loop 238, the gaseous chlorine sample is returned to the valve 214 through port 228, passes through passageway 220 and exits the valve 214 through port 226 into the return line 54 wherein the sample is fed back into the process stream.

Also during the deactive period, a first carrier gas stream from the carrier gas storage tank 298 flows from the tank 298 through line 288 and the first carrier gas stream line 290 to the port 258 of the backflush valve 250 where it passes through the passage 274 and exits the valve 250 through the port 256. The first carrier gas stream then flows through the line 246 to the sampling valve 214, where it enters the port 230, passes through the passage 224 and exits the valve 214 through the port 236 into the line 244 containing the first chromatographic column 248. The first carrier gas stream then flows through the first chromatographic column 248 and returns to the backflush valve 250 where it enters the valve 250 through the port 264, passes through passage 278 and exits the valve 250 through the port 266 into the line 280 containing the second chromatographic column 304.

The first carrier gas stream then passes through the second chromatographic column 304 and enters the storage valve 306 through the port 314. In the valve 306, the first carrier gas stream passes through passage 330, exits the valve 306 through port 312 and passes through the loop 344 containing the molecular sieve column 346 and reenters the valve 306 through port 320. The first carrier gas stream then passes through passage 334 in the valve 306 and exits the valve 306 through the port 322 into the carrier-sample flow line 338 through which it flows to the detector 339 and exits the detector into the waste line 348 to the caustic scrubber 350.

Thus, in the deactive or loading position of the analyzer 16, a gaseous chlorine sample from the process stream which has been converted to gaseous form by the vaporizer 12, continuously flows through the sample loop 238 and back to the process stream. At the same time, the first carrier gas stream passes through the two chromatographic columns 248 and 304, the molecular sieve column 346 and the detector 339. This flow of carrier fluid serves to purge the chromatographic columns 248 and 304, the molecular sieve column 346 and the detector 339 of any sample remaining from the previous analysis. As will be noted, in the deactive position of the valves, the flow of the second carrier gas stream in the line 292 is blocked or cut off by the backflush valve 250.

When it is desired to perform an analysis, immediately prior thereto, the sample cut-off valve 202, under the control of microprocessor 203, is actuated into its activated position which serves to cut off the flow of gaseous chlorine sample to the sampling valve 214. This permits the gaseous chlorine sample in the sample loop to depressurize. After a short period of time sufficient to accomplish the depressurization, the sampling valve 214 is actuated into its activated position to start the analysis, while the backflush valve 250 and storage valve 306 remain in their deactive positions. The position of the valves 202, 214, 250 and 306 at this stage of the analysis is shown in FIG. 5.

Figure 5:
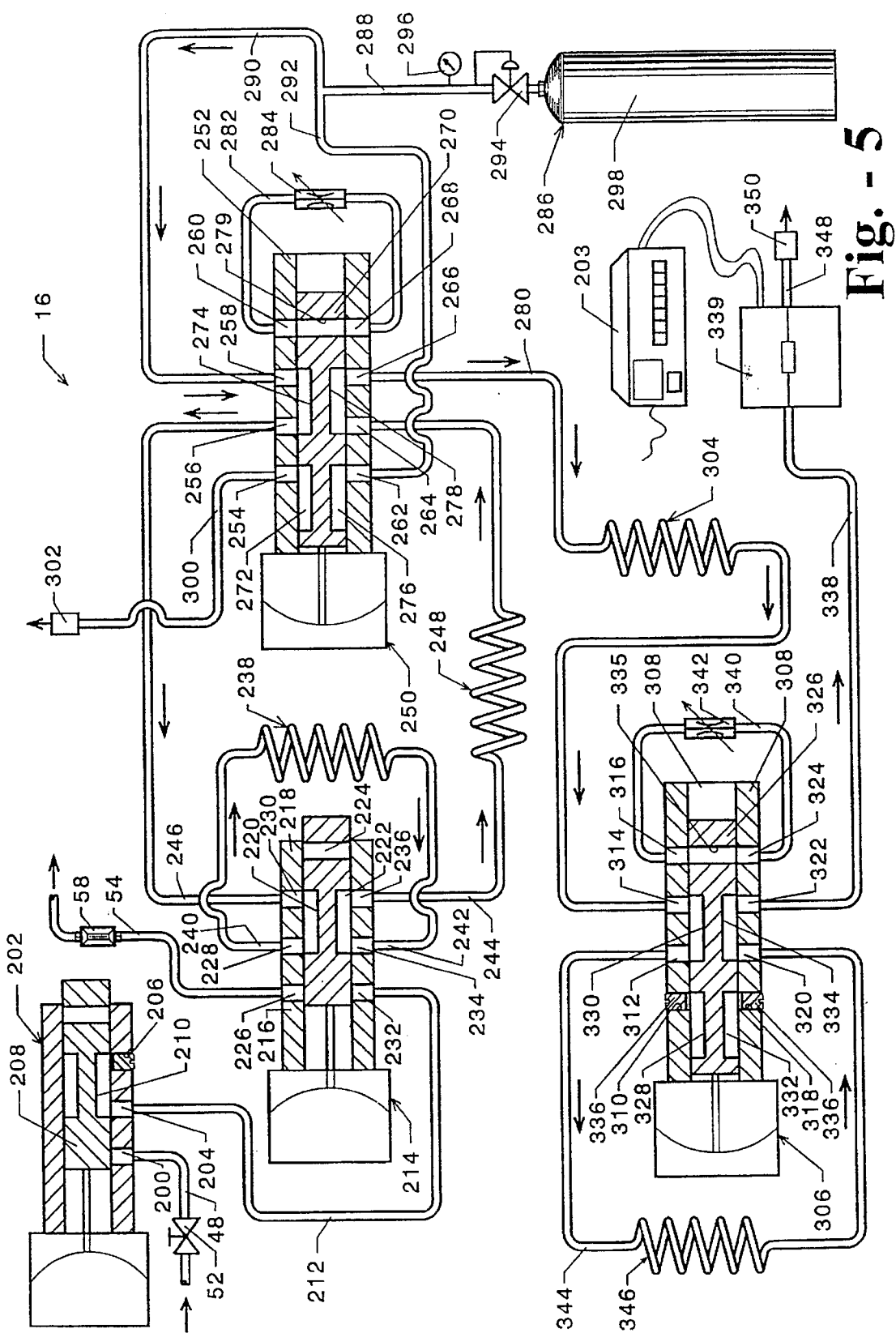
FIG. 5 is a schematic diagram of the analyzer shown in FIG. 4 showing the positions of the valves and flow through the system during one stage of the sampling cycle.

With the valves 202, 214, 250 and 306 positioned as shown in FIG. 5, the first carrier gas stream in line 246 enters port 230 of the sampling valve 214, passes through passage 220, exits port 228 and passes through the sample loop 238, carrying with it the chlorine sample in the loop 238. The first carrier gas stream transports the chlorine sample from the loop 238 back into the valve 214 through the port 234, and then through the passage 222, and out through the port 236 of the valve 214 into the line 244 containing the first chromatographic column 248. The carrier gas continues to transport sample from the first chromatographic column 248 through the backflush valve 250 by way of the port 264 and the passage 278 and out through the port 266 into the line 280 containing the second chromatographic column 304. The first carrier gas stream with sample continues into the storage valve 306 through port 314, passes through the passage 330 and exits the valve 306 through the port 312 into the storage loop 344 containing the molecular sieve column 346. From the storage loop 344, the carrier gas continues back into the storage valve 306 through the port 320, passes through the passage 334, and exits the valve 306 through the port 322 into line 338 where the carrier gas passes through the detector 339 and then to the line 348 to the caustic scrubber 350.

During the passage of the first carrier gas stream and sample through the first chromatographic column 248, the column 248 serves to separate the chlorine from the other gases, specifically oxygen, nitrogen and carbon dioxide, with the oxygen and nitrogen being separated as bulk from the chlorine and carbon dioxide. Chlorine, being the heaviest material is never allowed to exit the first chromatographic column 248. The oxygen and nitrogen, being the lightest, pass through the column 248 first, followed by the carbon dioxide, and into the second chromatographic column 304 where the separation of the oxygen and nitrogen from the carbon dioxide is completed. The oxygen and nitrogen from the second chromatographic column 304 are allowed to enter the molecular sieve column 346 by passing through the port 314 of the storage valve 306, passing through the passage 330, and exiting the valve 306 through the port 312 into the loop 344 containing the molecular sieve column 346. As soon as the oxygen and nitrogen enter into the molecular sieve column 346, the storage valve 306 is moved into its activated position. The position of the valves 202, 214, 250 and 306 after the storage valve 306 is activated is shown in FIG. 6.

Figure 6:
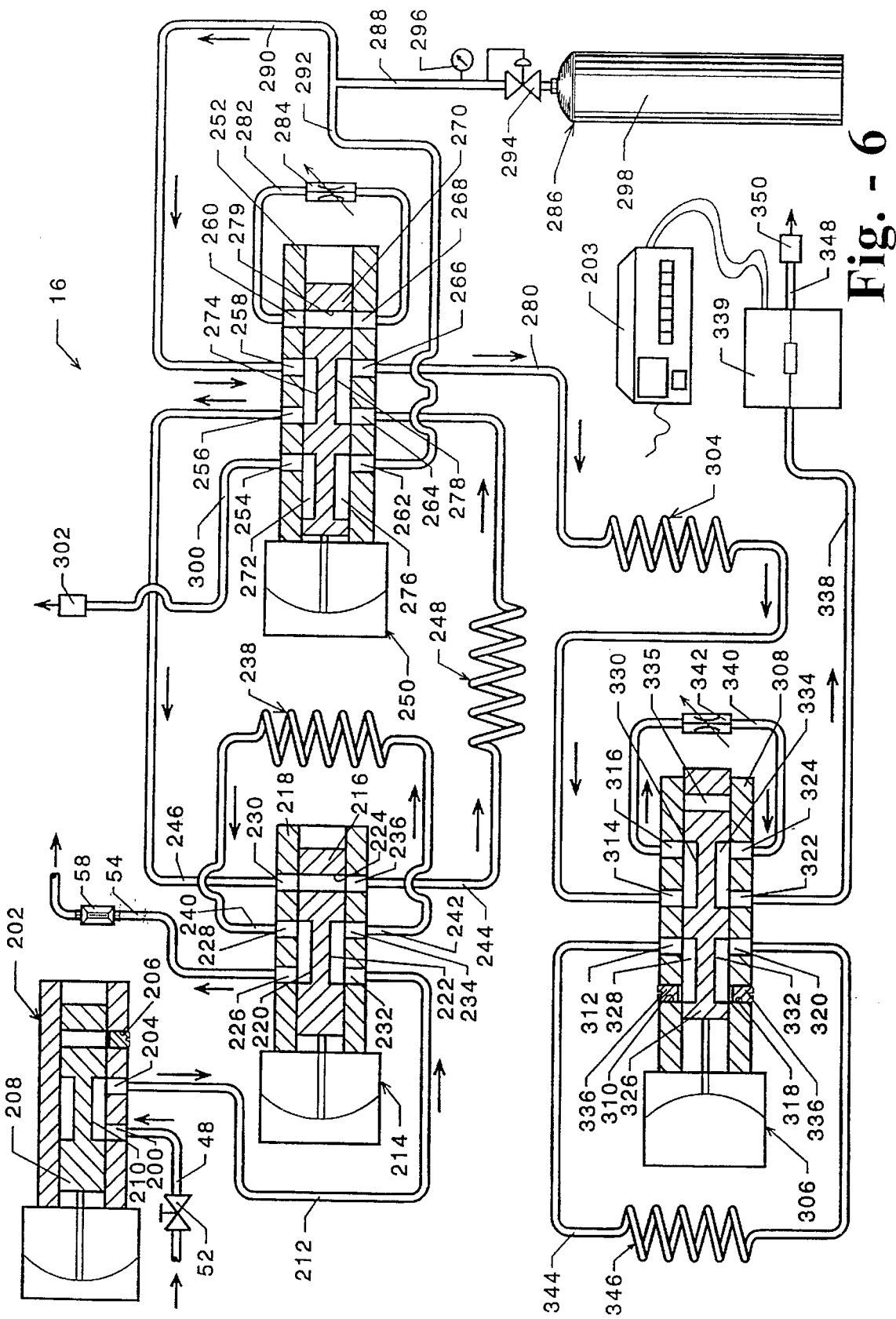
FIG. 6 is a schematic diagram of the analyzer shown in FIG. 4 showing the positions of the valves and flow through the system during another stage of the sampling cycle.

As shown in FIG. 6, by this stage of the analysis, the sample cut-off valve 202 and the sampling valve 214 may be returned to their inactive positions. The backflush valve 250 remains in its inactive position and the storage valve 306 has been actuated into its activated position. When the storage valve 306 is activated, the ports 312 and 320 of the valve 306 are effectively blocked since the passages 328 and 332 in the slider plate 308 now provide communication between the port 312 and a blocked port 310 and the passage 332 provides communication between port 320 and blocked port 318. This serves to trap the oxygen and nitrogen in the molecular sieve column 346.

The activation of the storage valve 306 also results in the first carrier gas stream with the sample flowing in line 280 from the second chromatographic column into port 314 of the storage valve 306 being diverted so that it flows through passage 330 in the valve 306, out of the valve 306 through port 316, through the restrictor 342 and back into the valve 306 through port 324. The first carrier gas stream with sample then passes through passage 334 and exits the valve 306 through port 322 into line 338 to the detector.

Figure 7:
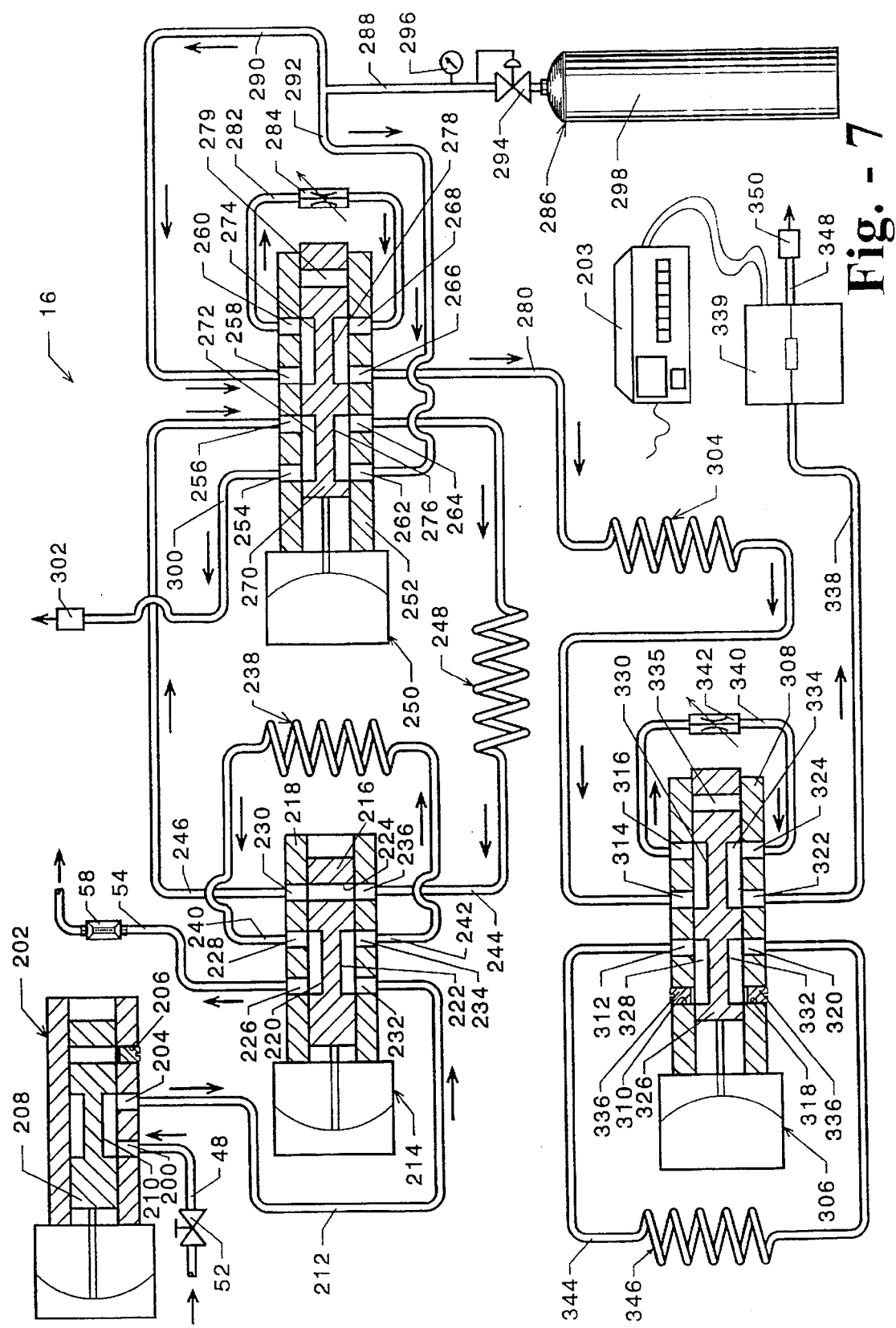
FIG. 7 is a schematic diagram of the analyzer shown in FIG. 4 showing the positions of the valves and flow through the system during a further stage of the sampling cycle.

After the storage valve 306 is activated, and as soon as all the carbon dioxide is carried out of the first chromatographic column 248 and into the second chromatographic column 304, the backflush valve 250 is activated while the sample cut-off valve 202 and the sampling valve 214 remain deactive, so that the valves assume the positions as shown in FIG. 7. In this position of the valves 202, 214, 250 and 306, the first carrier gas stream from line 290 is caused to bypass the sampling valve 214 and the first chromatographic column 248, and pass through the restrictor 284 associated with the backflush valve 250, through the second chromatographic column 304, through the restrictor 342 associated with the storage valve 306 to the detector 339 to carry the carbon dioxide from the second chromatographic column 304 to the detector 339 for measurement by the detector 339 as the first component of the sample.

As will be seen from FIG. 7, this is achieved by the fact that upon activation of the backflush valve 250, the first carrier gas stream enters the backflush valve 250 through port 258 from line 290 and is diverted by the passage 274 to the port 260 from which its exits into the loop 282 containing the restrictor 284. From the restrictor 284, the second carrier gas stream reenters the valve 250 through port 268, passes through passage 278 and exits the valve 250 through port 266 into the line 280 containing the second chromatographic column 304. After passing through the second chromatographic column 304 and carrying with it the carbon dioxide in the column 304, the first carrier gas stream enters the storage valve 306 through port 314, passes along the passage 330, and exits the valve 306 through the port 316 into the restrictor line 340 containing the restrictor 342. After passing through the restrictor 342, the first carrier gas stream containing the carbon dioxide to be measured reenters the valve 306 through the port 324, passes through passage 334 and exits the valve 306 through port 322 into the line 338 to the detector 339. As the sample passes through the detector 339, the detector generates an electrical signal proportional to the amount of carbon dioxide present in the sample which is fed to the microprocessor 203. The microprocessor 203 converts the electrical signal from the detector 339 into a signal indicative of the actual level of carbon dioxide. This signal may then be fed to the data acquisition network 20 for recording and display.

The restrictor 284 associated with the backflush valve 252 serves to reduce the flow rate of the first carrier gas stream to the second chromatographic column 304 when the backflush valve 250 is in its activated position. This is necessary since the first carrier gas stream is under a sufficiently high pressure from its source so it will have a flow rate sufficient to overcome the resistance to flow of the first chromatographic column 248 when the backflush valve 250 is deactive and the carrier stream passes through the first column. Since the first carrier gas stream bypasses the first chromatographic column 248 when the backflush valve 250 is activated, the flow rate of the first carrier gas stream must be reduced an amount substantially the same as it would be by the chromatographic column 248 or the flow rate of the first carrier gas stream will be too high as it passes through the second chromatographic 304 and ultimately through the detector 339 to permit an accurate measurement. Accordingly, the restrictor 284 should be set to provide a reduction in flow rate of the first carrier gas stream substantially equivalent to the reduction which is caused by the first chromatographic column.

In a similar manner, the flow restrictor 342 in the loop 340 connected to the storage valve 306 serves to reduce the flow rate of the first carrier gas stream when the storage valve 306 is in its activated position and the first carrier gas stream bypasses the molecular sieve column 346. The flow restrictor 342 should be set so that the flow rate of the first carrier gas stream entering line 338 from the valve 306 is the same when it bypasses the molecular sieve column 346 as it is when it passes through the molecular sieve column 346. Thus, the flow restrictors 284 and 342 serve to maintain the flow rate of the first carrier gas stream to the detector 339 at a constant rate whether the first carrier gas stream passes through the first chromatographic column 248 and the molecular sieve column 346 or whether it bypasses one or both of them.

Additionally, when the backflush valve is activated, as shown in FIG. 7, the second carrier gas stream flows through line 292 to the backflush valve 250 and enters the valve 250 through the port 262. The second carrier gas stream then passes through passage 276 in the backflush valve 250 and out of the valve 250 through the port 264. The second carrier gas stream then flows backward in the line 244 through the first chromatographic column 248 and carries the chlorine in the column 248 with it into port 236 of the sampling valve 214. The second carrier gas stream along with the chlorine that was present in the first chromatographic column 248 then passes through the through-bore 224 in the valve 214 and exits through port 230 into the line 246. The second carrier gas stream and the chlorine enter the port 256 of the valve 250 from the line 246, pass through the passage 272 and exit the valve 250 through the port 254 into line 300 to the caustic scrubber 302. Thus, when the backflush valve 250 is actuated, the first chromatographic column 248 is backflushed to remove the chlorine therefrom and carry it out of the system to the caustic scrubber 302.

Figure 8:
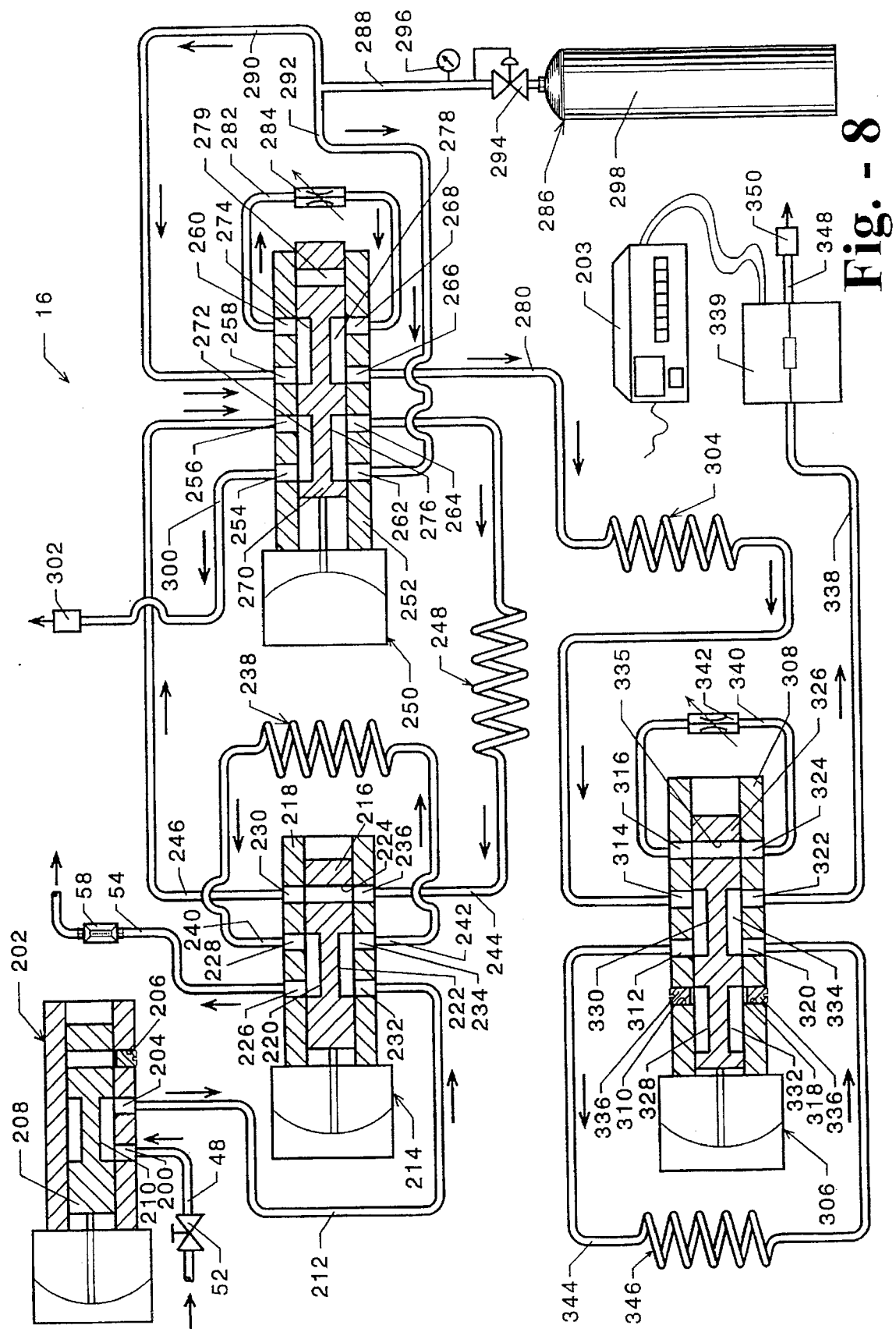
FIG. 8 is a schematic diagram of the analyzer shown in FIG. 4 showing the positions of the valves and flow through the system during the latter stage of the sampling cycle.

After the measuring and recording of the carbon dioxide level by the detector 339, the storage valve 306 is deactivated while the backflush valve 250 is maintained in its activated position. The valves 202, 214, 250 and 306 at this stage are in the positions as shown in FIG. 8. As may be seen from FIG. 8, the first carrier gas stream continues to flow through the restrictor 284 associated with the backflush valve 250 and the second chromatographic column 304 and enters the storage valve 306 through the port 314. With the storage valve 306 now in its deactive position, the first carrier gas stream then passes through the passage 330 and out through port 312 of the valve 306 into the line 344 containing the molecular sieve column 346. The carrier gas passes through the molecular sieve column 346, carrying the oxygen and nitrogen, which now have been completely separated by the column 346, back into the valve 306 through the port 320. The first carrier gas stream carrying the oxygen and nitrogen then passes through passage 334 of the valve 306 and out of the valve 306 through port 322 into the line 338 in which the oxygen and nitrogen are carried to the detector 339 for measurement as components two and three of the sample, respectively. After the measuring of the oxygen and nitrogen, the backflush valve 250 may be deactivated, resulting in all the valves 202, 214, 250 and 306 being in their deactive positions as shown in FIG. 4, ready for another analysis by repeating the analytical cycle described above.

While not specifically shown in the drawings, the various valves 202, 214, 250 and 306, the carrier fluid source 286, the sample loop 238, the chromatographic columns 248 and 304, the molecular sieve column 346 and detector 339, as well as the associated piping, are all maintained in a temperature controlled environment with the appropriate temperature being maintained by suitable heating means such as a forced air or electric heater. This ensures that there will not be any variations in temperature after the system has been calibrated which would effect their accuracy of the readings from one analysis to another.

The timing of the actuation of the individual valves between their deactive and activated positions may be determined experimentally upon initial calibration of the analyzer 16. Such initial calibration may be achieved introducing a calibration chlorine sample containing a known amount of the non-condensable gases into the sample loop and starting the cycle. The time at which the various gases elute from the various column combinations and are passed to the detector 339 is noted and the actuation of the various valves 202, 214, 250 and 306 set accordingly to achieve the complete separation of the components. By using a sample of a known quantity of the various non-condensable gases, the microprocessor may be adjusted to reflect the actual concentration of each individual component of the sample which will provide the set points for the other concentrations.

By way of example, the system as shown in FIG. 4–8 may be operated using a 10 foot length of ¼" tubing of 15% SF-96 on Chromosorb® W for the first chromatographic column 248, a 10 foot length of ¼' tubing containing HayeSep® R powder as the second chromatographic column, and a 10 foot length of ¼" tubing containing a 5 Å molecular sieve as the molecular sieve column 346. The chromatographic columns 248 and 304, and the molecular sieve column 346 may be maintained at a temperature of 75° C. The carrier gas may be high purity helium having a flow rate of 50 ml/min. The detector may be a Model 24-600 discharge ionization detector as described above.

With the arrangement as described immediately above, the analytical cycle is about 1500 seconds. Assuming that the cycle starts when the sampling valve 214 is actuated into its activated position, the sample cut-off valve 202 is first actuated about 25 seconds before the actual start of the cycle. This permits time for the sample in the sample loop 238 to depressurize. After approximately 25 seconds, at a time equal zero, the sampling valve 214 is actuated to start the cycle. After about 10 seconds into the cycle, giving time for the carrier gas stream to remove the sample from the sample loop 238, the sampling valve 214 is moved back into its deactive position followed by the actuation of the sample cut-off valve 202 into its deactive position at about 15 seconds into the cycle. The exact time point for actuating the sample cut-off valve 202 and the sampling valve 214 back into their deactive positions is not critical so long as the sampling valve 214 is deactivated prior to the activation of the backflush valve 250. The sampling valve 214 should preferably be moved to its inactive position slightly prior to the actuation of the cut-off valve 202 into its deactive position so that the sample from the cut-off valve 202 will have a path through the sample valve 214.

The storage valve 306 is actuated into its activated position at about 245 seconds into the cycle. The elution of the carbon dioxide occurs between about 250 and 545 seconds into the cycle so that the backflush valve 250 is actuated into its activated position at about 550 seconds. The storage valve 306 is then actuated into its deactive position opening the storage loop 344 to the carrier fluid at about 613 seconds. The oxygen elution occurs between about 620 and 818 seconds into the cycle and nitrogen elution occurs between about 825 and 1090 seconds. The backflush valve 250 may be actuated into its deactive position at about 1470 seconds into a position to start the next cycle.

Figure 9:
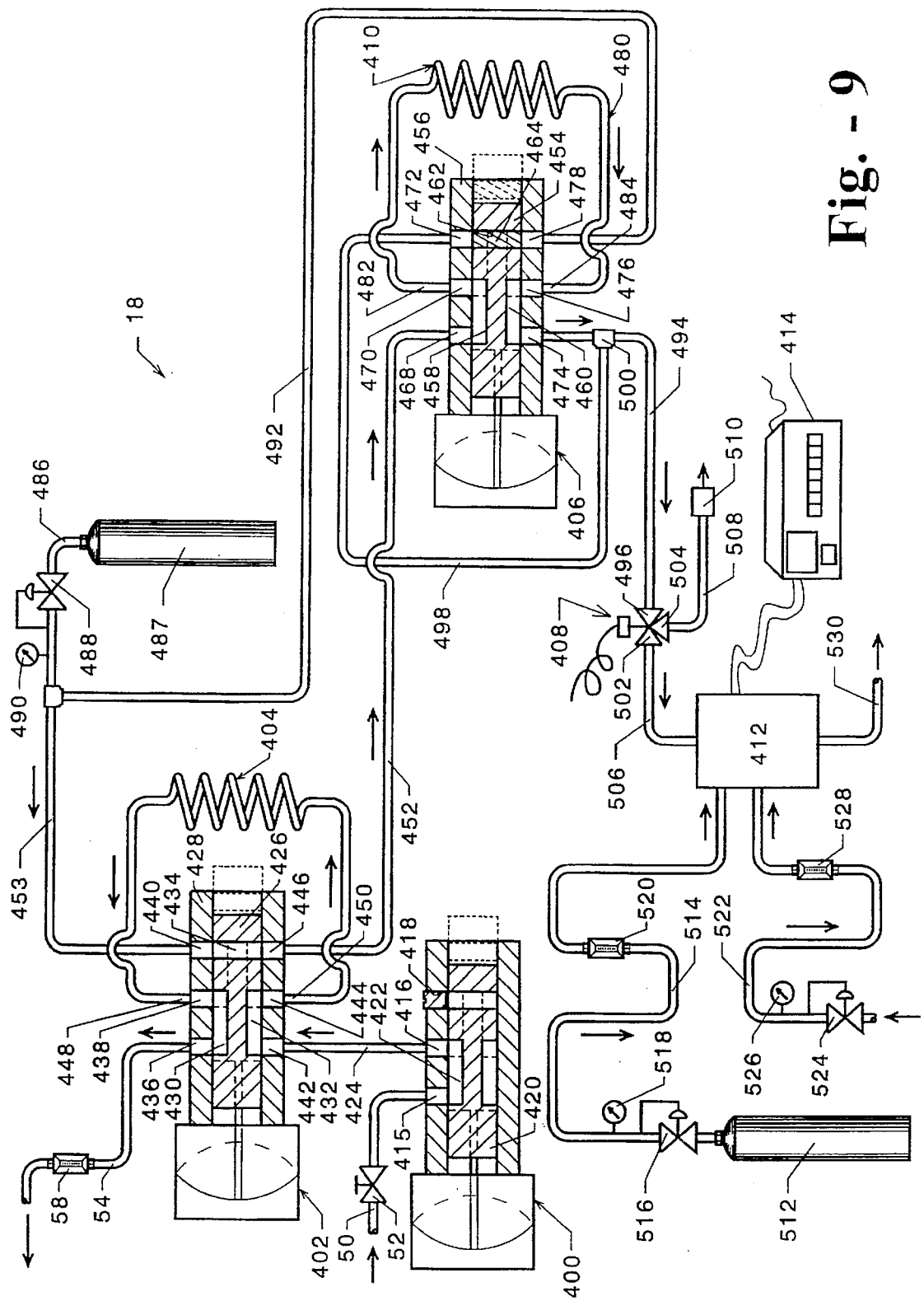
FIG. 9 is a schematic diagram of the portion of the system of FIG. 1 comprising the analyzer for the detection and measurement of halocarbons in chlorine, and showing the position of the valves and flow through the system while the system is inactive.
Figure 10:
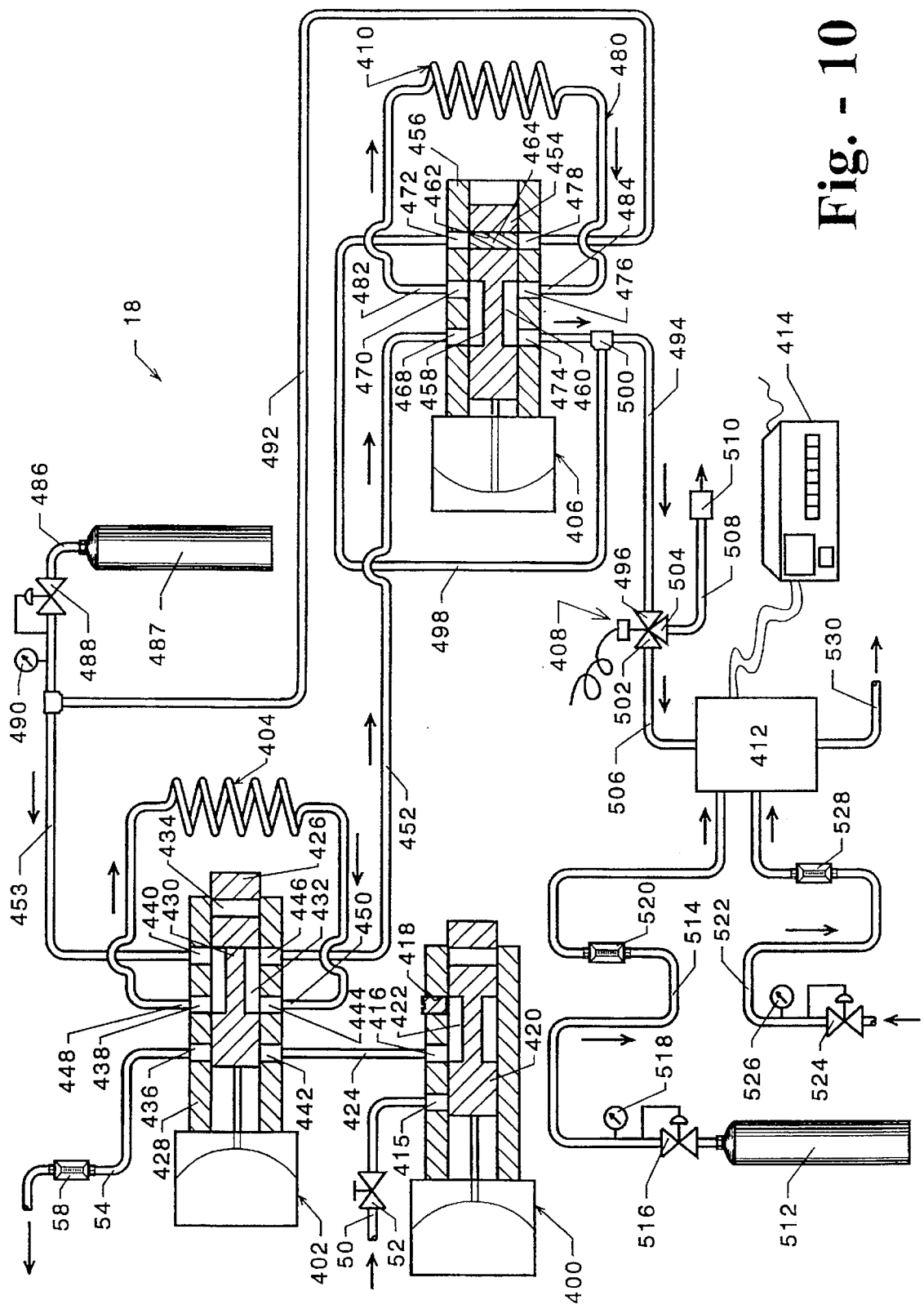
FIG. 10 is a schematic diagram of the analyzer shown in FIG. 9 showing the positions of the valves and flow through the system during one stage of the sampling cycle.
Figure 11:
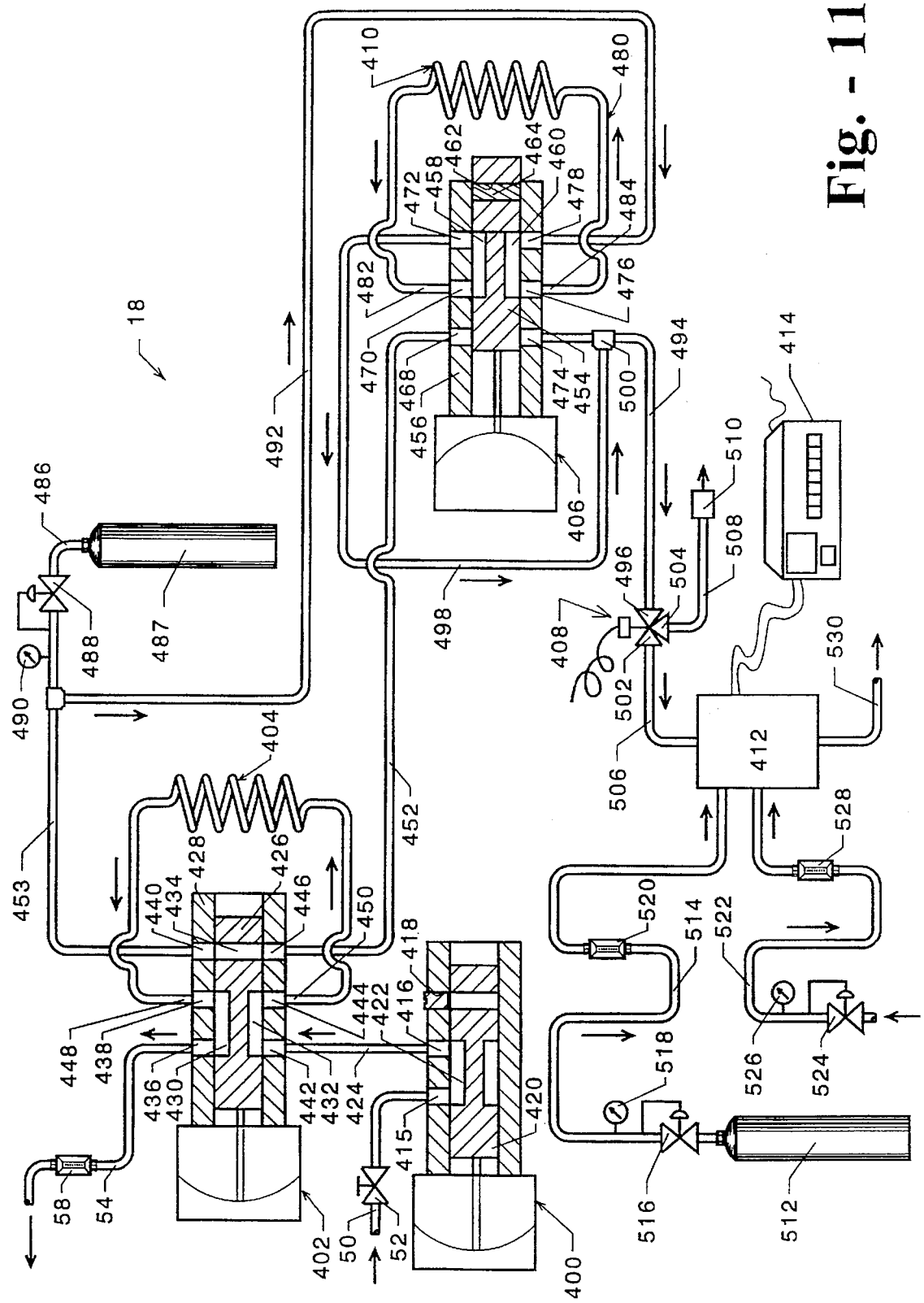
FIG. 11 is a schematic diagram of the analyzer shown in FIG. 9 showing the positions of the valves and flow through the system during another stage of the sampling cycle.

The halocarbon in chlorine analyzer 18, shown schematically in FIGS. 9–11, is adapted to measure chlorinated hydrocarbons which may be present in the chlorine sample, and specifically methylene chloride, chloroform and carbon tetrachloride. All other chlorinated hydrocarbons which could be potentially present in the chlorine sample are measured as a group.

The halocarbon in chlorine analyzer 18 includes generally a sample cut-off valve 400 for cutting off the supply of chlorine sample from the process stream, a sampling valve 402 for feeding the sample from the process stream to a sample loop 404, a backflush valve 406 for controlling the flow of a carrier gas, a diverter valve 408 for diverting the chlorine to prevent its passage to the detector, a chromatographic column 410 for separating the components of the sample stream; a detector 412 for detecting and measuring the desired components of the sample, and a microprocessor 414 for controlling the timing of the analytical cycle and converting the-signals from the detector 412 into readable output.

Specifically, referring to FIG. 9, the chlorine sample enters the analyzer through the line 50 and valve 52 into a port 415 of the cut-off valve 400. The cut-off valve 400 may be of any type of electrically actuated, on-off valve that may be controlled by the microprocessor 414. Preferably, the valve 400 is a modified pneumatically operated six-port slider plate valve controlled by a solenoid valve (not shown) and is similar to the cut-off valve 202 described in connection with the analyzer shown in FIGS. 4–8. The valve 400 includes two active ports 415 and 416, and a blocked port 418. A moveable slider plate 420 within the valve 400 has a groove or passage. 422 which interconnects the port 415 with the port 416 when the valve 0 is in its deactive position as indicated by the solid lines in the drawing. When the valve 400 is activated, the slider plate 420 is moved into the off-position shown by the dotted lines in the drawing, wherein the passage 422 is out of alignment with the port 415 and there is no communication, and thus, no flow between the ports 415 and 416.

The port 416 of the valve 400 has one end of a sample in-feed line 424 connected thereto. The other end of the sample infeed line 424 is connected to the sampling valve 402.

The sampling valve 402 may be similar to the sampling valve 214 shown and described in connection with the non-condensable gas in chlorine analyzer 16 of FIGS. 4–8. The sampling valve 402 may be a standard, commercially available, 6-port sliding plate valve which is pneumatically actuated between a deactive or sample loading position and an activated or sample injecting position. A solenoid valve (not shown), controlled by the microprocessor 414, may control the supply of the pneumatic fluid such as instrument air to the valve 402 to cause the movement of the valve 402 between its two positions.

The sampling valve 402 may include a slider plate 426 movable in a body 428 between the two positions of the valve 2. The slider plate 426 may include a first groove or passage 430 which extends axially in the top surface of the slider plate 426 as viewed in FIG. 9. A second groove or passage 432 may extend axially in the bottom surface of the slider plate 426. A through-bore or passage 434 is provided in the slider plate 426 extending between the top and bottom surfaces thereof.

The body 428 of the sampling valve 402 may include six ports 436, 438, 440, 442, 444 and 446, with ports 436, 438 and 440 being positioned in the top surface of the body 428 and ports 442, 444 and 446 being positioned in the bottom surface of the body 428 when the valve 402 is spatially positioned as shown in FIG. 9.

The deactive or loading position of the sampling valve 402 is indicated by the solid lines of the slider plate 426 as shown in FIG. 9 and the activated, or injecting position by the dotted lines of the slider plate 426. In the deactive or loading position, the passage 430 connects the ports 436 and 438, while passage 432 connects the ports 442 and 444. The through-bore or passageway 434 connects the ports 440 and 446. When the valve 402 is activated, the slider plate 426 is moved to the right as viewed in FIG. 9 into the activated or injecting position, assuming the position indicated by the dotted lines. In the activated or injecting position of the valve 402, the passage 430 connects the ports 438 and 440 and the passage 432 connects the ports 444 and 446, while the ports 436 and 442 are blocked. The through-bore 434 is not active in the activated position of the sampling valve 404.

The sample infeed line 424 from the sample cut-off valve 400 is connected to the port 442 of the sampling valve 402. The sample return line 54 with the flow meter 58 therein is connected to the port 436. The sample loop 404 has one end 448 connected to the port 438 and its other end 450 connected to the port 444. A carrier-sample outlet line 452 is connected to the port 446 of the sampling valve 402 and a first carrier stream line 453 is connected to the port 440.

The carrier-sample outlet line 452, connected at one end to the sampling valve 402, has its other end connected to the backflush valve 406. The backflush valve 406 is a specially modified, pneumatically operated, six port sliding plate valve which is pneumatically actuated between a deactive and an activated position. An electrically operated solenoid valve (not shown) may be used to control the supply of pneumatic fluid such as instrument air to the valve 406 to cause the actuation of the backflush valve 406 between its two positions. The solenoid valve may in turn be controlled by the microprocessor 414.

The backflush valve 406 may include a slider plate 454 movable in a body 456 between the two positions of the valve. The slider plate 454 may include a first groove or passage 458 which extends axially in the top surface of the slider plate 454 as view in FIG. 9. A second groove or passage 460 may extend axially in the bottom surface of the slider plate 454. A through-bore or passage 462 is usually provided in the slider plate 454 extending between the top and bottom surfaces thereof. However, this through-bore 462 is plugged by an insert 464. Alternatively, the slider plate may be fabricated without the through-bore 464.

The body 456 of the backflush valve 406 may include six ports 468, 470, 472, 474, 476 and 478, with ports 468, 470 and 472 being positioned in the top surface of the body 456 and ports 474, 476 and 478 being positioned in the bottom surface of the body 456 when the valve 406 is spatially positioned as shown in FIG. 9.

The deactive position of the backflush valve 406 is indicated by the solid lines of the slider plate 454 in FIG. 9 and the activated position indicated by the dotted lines of the slider plate 454. In the deactive position of the valve 406, the passage 458 connects the ports 468 and 470, while passage 460 connects the ports 474 and 476. The ports 472 and 478 are effectively blocked by the insert 464 in the through-bore or passage 462. When the valve 406 is activated, the slider plate 454 is moved to the right as viewed in FIG. 9, assuming the position indicated by the dotted lines. In this activated position, the passageway 458 connects the ports 470 and 472 and the passageway 460 connects the ports 476 and 478, while the ports 468 and 474 are blocked. The backflush valve 406 has thus been modified from the standard configuration so that although it includes the six ports 468, 470, 472, 474, 476 and 478, it only has two passageways 458 and 460 for providing communication between the ports, resulting in one set of ports 472, 478 being rendered inactive in one position of the valve 6 and a second set of ports 468, 474 being rendered inactive in the other position of the valve.

A chromatographic loop 480, containing the chromatographic column 410 has one end 482 connected to the port 470 of the backflush valve 6 and its other end 484 connected to the port 476 of the valve 6. The chromatographic column 410 is one that separates methylene chloride, chloroform and carbon tetrachloride from each other and from the chlorine. The preferred form of the column is a 4 foot length of ¼ inch coiled tubing packed with acid washed Chromosorb® W impregnated with 40% Kel-F® oil, a chlorofluorocarbon oil, and maintained at a temperature of 60° C.

A line 486 is attached to a source of a carrier gas. The carrier gas may be any suitable type of gas which will not react with any of the components in the sample stream, does not contain any of the components for which the analysis is being made, and which does not interfere with the detection and measurement by the detector or with the separation of the components in the chromatographic column 410. More specifically, the carrier gas may be any suitable inert gas. Preferably, the carrier gas is helium supplied from suitable storage tank 487 to which the line 486 is connected.

The line 486 includes a pressure regulator 488 and pressure gauge 490 to control the flow of the helium and provide an indication of its pressure. Preferably, the flow rate of the helium is relatively slow, about 55 milliliters per minute (ml/min). The line 486 branches into two carrier stream lines, the first carrier gas stream line 453 which is connected to the port 440 of the sampling valve 402, and a second carrier gas stream line 492 which is connected to the port 478 of the backflush valve 406.

A carrier-sample output line 494 has one end connected to the port 474 of the backflush valve 406 and its other end connected to an inlet 496 of the diverter valve 408. A reverse flow sample output line 498 has one end connected to the port 472 and its other end connected to the carrier-sample output line 494 at a "T" 500 positioned upstream of the diverter valve 408 and adjacent to the port 474 of the backflush valve 406.

The diverter valve 408 may be any type of valve which can be electrically controlled by the microprocessor 414 to divert the flow entering its inlet 496 to either of its two output ports 502 and 504. Preferably, the diverter valve 408 is a solenoid actuated, 3-port sliding plate valve. The output port 502 of the diverter valve 408 is connected to a line 506 which in turn is connected to the detector 412. The other output port 504 is connected to a line 508 leading to a caustic scrubber 510.

The detector 412 is preferable a flame ionization detector. The detector 412 may be any commercially available flame ionization detector capable of detecting and measuring the desired components. An example of one such detector is the GOW-MAC FID System Model No. 40-900 by Gow-Mac Instrument Co. As is common with such detectors, fuel is supplied to the detector which in the preferred case may be hydrogen and air. The hydrogen may be supplied from a suitable source such as a storage tank 512 through a line 514 containing a pressure regulator 516 to maintain the desired pressure and a pressure gauge 518 and flow meter 520 which provide an indication of the pressure and flow of the hydrogen respectively. The air may be supplied to the detector 412 from a suitable source such as available plant air through a line 522 containing a pressure regulator 524 to maintain the desired pressure and a pressure gauge 526 and flow meter 528 which provide an indication of the pressure and flow of the air respectively.

The flame ionization detector 412 ionizes the separated chemical components eluting from the chromatographic column 410 and which enter the detector 412 from line 506. The ionized components collect at a collector plate (not shown) in the detector 412 and a current is generated proportional to the amount of the individual component being detected. The current signal is transmitted to the microprocessor 414, which converts the signal into a readable form indicative of the concentration of the particular component. The microprocessor 414 sends the data collected to the common data acquisition network 20 for tabulation and printout. The combusted sample exits the detector 412 through an output line 530 to a vent.

In operation, the sample cut-off valve 400, the sampling valve 402 and the backflush valve 406 are maintained in their deactive positions until it is desired to begin an analysis. The operation of the analysis cycle is controlled by the microprocessor 414.

In the deactive positions of the valves 400, 402 and 406, the chlorine sample in gaseous form from the vaporizer 12 flows into the sample cut-off valve 400 through port 415, flows through passage 422 and out of the cut-off valve 400 through port 416 into the feed line 424 leading to the sampling valve 402.

The gaseous chlorine sample enters the sampling valve 402 from the feed line 424 through the port 442, passes through the passage 432 and exits the valve 402 through the port 444 into the sample loop 404. From the sample loop 404, the gaseous chlorine sample is returned to the valve 402 through the port 438, passes through the passage 430 and exits the valve 402 through the port 436 into the return line 54 wherein the sample is fed back into the process stream at a low pressure point.

Also during the deactive period, a first carrier gas stream from the carrier gas storage tank 487 flows through the line 486 and the first carrier gas stream line 453 to the port 440 of the sampling valve 402 where it passes through the passage 434 and exits the valve 402 through the port 446 into the line 452 to the backflush valve 406. The first centers gas stream then enters the port 468 of the backflush valve 406, passes 10 through the passage 458 and exits the valve 406 through the port 470 into the chromatographic loop 480 containing the chromatographic column 410. The first carrier gas stream then flows through the chromatographic column 410 and returns to the backflush valve 406 where it enters the valve 406 through port 476. The first carrier gas stream then passes through the passage 460 and exits the valve 406 through the port 474 into the line 494 to the diverter valve 408. The diverter valve 408 at this stage of the analysis is in its inactive position which provides for flow through the valve 408 and out through the outlet 502 to line 506. The first carrier gas stream passes through the diverter valve 408 into the line 506 through which it flows to the detector 412 and then exits the detector 412 into the line 530 to the vent.

Thus, in the deactive or non-detecting position of the valves 400, 402, 406 and 408, a gaseous chlorine sample from the process stream which has been vaporized by the vaporizer 12 continuously flows through the sample loop 4 and back to the process stream. At the same time, a first carrier gas stream passes through the chromatographic column 410 and the detector 412. This flow of carrier gas serves to purge the chromatographic column 410 and detector 412 of any sample remaining from the previous analysis. As will be noted, in the deactive position of the valves, the flow of the second carrier gas stream from the storage tank 487 is blocked or cut off by virtue of the insert 464 provided in the passage 462 of the backflush valve 406.

When it is desired to perform an analysis, immediately prior thereto the sample cut-off valve 400, under the control of the microprocessor 414, is activated into its activated position which serves to cut off the flow of gaseous chlorine sample to the sampling valve 402. This permits the gaseous chlorine sample in the sample loop 404 to depressurize. After a short period of time sufficient to accomplish the depressurization, the sampling valve 402 is actuated into its activated position to start the analysis. The position of the valves 400, 402 and 406 at this stage of the analysis is shown in FIG. 10.

With the valves 400, 402 and 406 positioned as shown in FIG. 10, the first carrier gas stream in line 453 enters the port 440 of the sampling valve 402, passes through the passage 430, exits the port 438 and passes through the sampling loop 404, carrying with it the chlorine sample in the sample loop 404. The carrier gas transports the sample from the loop 404 back into the valve 402 through the port 444, and then through passage 432, and out of the valve 402 through the port 446 into the line 452 to the backflush valve 406.

The first carrier gas stream continues to carry the sample into port 468 of the backflush valve 406, through the passage 458 and out of the valve 406 through the port 470 into the chromatographic column 410. The column 410 serves to separate the components of the sample into methylene chloride, chloroform, and carbon tetrachloride, chlorine and other chlorinated hydrocarbons. The chlorine elutes first from the chromatographic column 410 and is carried by the first carrier gas stream from the column 410 into the backflush valve 406 through the port 476, where it passes through the passage 460 and exits the valve 6 through the port 474 into the line 494 to the diverter valve 408.

Immediately prior to the elution of the chlorine from the chromatographic column 410, the diverter valve 408 is actuated into it activated position. The chlorine being carried by the first carrier gas stream in the line 494 flows into the diverter valve 408 and is diverted out thorough the outlet 504 into the line 508 and passes to the caustic scrubber 510. Thus, the chlorine is never permitted to enter the detector 412.

The methylene chloride, chloroform and carbon tetrachloride are separated by the chromatographic column 410 in that order. These components follow the chlorine out of the column 410, through the port 476 into the backflush valve 406, through the passage 460 and out of the valve 406 through the port 474 into the line 494. As soon as all the chlorine has been diverted by the diverter valve 408 to the scrubber 510, the diverter valve 408 is deactivated into its deactive position. The carrier gas then carries the methylene chloride, chloroform and carbon tetrachloride from line 494 into the inlet 496 of the diverter valve 408 and out of the valve 408 through the outlet 502 into the line 506 where they flow to the detector 412 for detection and measurement by the detector 412 in that order.

After the elution of the methylene chloride, chloroform and carbon tetrachloride from the chromatographic column 410 and passage into line 494, the backflush valve 406 is actuated into its activated position. The positions of the valves 400, 402 and 406 after the backflush valve 406 is activated is shown in FIG. 11.

As shown in FIG. 11, by this stage of the analysis, the sample cut-off valve 400 and the sampling valve 402 may be returned to their inactive positions. The diverter valve 408 remains in its deactive position and the backflush valve 406 has been actuated into its activated position. With the valves in the positions shown, the first carrier gas stream, after passing through valve 402 into line 452, is blocked from flowing at port 468 of the backflush valve 406 by the slider plate 454. The second carrier gas stream now flows through the line 492 and enters the port 478 of the backflush valve 406. The second carrier gas stream then passes through passage 460 in the valve 406, out through port 476 and into the end 484 of the chromatographic loop 480. The second carrier gas stream flows backward through the chromatographic column 410 to the port 470 of the backflush valve 406. The backward flow continues through passage 458 of the valve 406, out through the port 472 into the line 498 to line 494. The flow of the second carrier gas stream continues in the line 494 to the diverter valve 408, which is inactive, and through the valve 408 into line 506 to the detector 412. With this reverse flushing action through the chromatographic column 410 by the second carrier gas stream, any other chlorinated hydrocarbons which might have been present in the original chlorine sample and which never exited the chromatographic column 410, will exit the column 410, regroup and be detected by the detector as a group. After a sufficient time has elapsed to detect and measure any hydrocarbons in the reverse flow, the backflush valve 406 is deactivated and the system is ready for the next analysis cycle.

While not specifically shown in the drawings, the various valves 400, 402, 406 and 408, the carrier fluid source 487, the sample loop 404, the chromatographic column 410, and detector 412, as well as the associated piping are all maintained in a temperature controlled environment with the appropriate temperature being maintained by suitable heating means such as a forced air or electric heater. This ensures that there will be no variations in temperature after the system has been calibrated which would effect their accuracy of the readings from one analysis to another.

The timing of the actuation of the individual valves 400, 402, 406 and 408 between their deactive and activated positions may be determined experimentally upon initial calibration of the analyzer 18. Such initial calibration may be achieved introducing a calibration sample of chlorine containing a known amount of the halocarbons into the sample loop and starting the cycle. The time at which the various halocarbons elute and are passed to the detector 412 is noted and the actuation of the various valves 400, 402, 406 and 408 set accordingly. By using a sample of a known quantity of the various halocarbons, the microprocessor 414 may be adjusted based upon the signal received from the detector 412 to reflect the actual concentration of each individual component of the sample which will provide the set point for the other concentrations.

By way of example, the system as shown in FIG. 9–11 may be operated using a 4 foot length of ¼" tubing of 40% Kel-F® oil on acid washed Chromosorb® W for the chromatographic column 410. The chromatographic column 410 may be maintained at a temperature of 60° C. The carrier gas may be high purity helium having a flow rate of 55 ml/min. The detector 412 may be a flame ionization detector of the type described above with hydrogen flow thereto of 45 ml/min and air flow thereto of 250 ml/min.

With the arrangement as described immediately above, the analytical cycle is about 780 seconds. Assuming that the cycle starts when the sampling valve 402 is actuated into its activated position, the sample cut-off valve 400 is first actuated into its activated position at about 30 seconds before the actual start of the cycle. This permits time for the sample in the sample loop 404 to depressurize. After approximately 30 seconds, at a time equal to zero, the sampling valve 402 is actuated into its activated position to start the cycle. After about 10 seconds into the cycle, giving time for the carrier gas stream to remove the sample from the sample loop 404, the sampling valve 402 is moved back into its deactive position followed by the actuation of the sample cut-off valve 400 into its deactive position at about 15 seconds into the cycle. The exact time point for actuating the sample cut-off valve 400 and the sampling valve 402 back into their deactive positions is not critical so long as they are deactivated a sufficient period of time before the next cycle to permit a new sample to flow into the sample loop 404. The sampling valve 402 should preferably be moved to its inactive position slightly prior to the actuation of the sample cut-off valve 400 into its deactive position so that the sample from the cut-off valve 400 will have a path through the sampling valve 402.

The elution of the chlorine from the chromatographic column 410 will occur between about 20 and 100 seconds into the cycle so that the diverter valve 408 is actuated into its activated position at about 15 seconds, a time prior to the chlorine reaching the diverter valve. The methylene chloride elution will occur between about 120 and 168 seconds into the cycle so that the diverter valve 408 is activated back into its deactive position at about 105 seconds to permit the methylene chloride to flow to the detector 412. Chloroform elution will occur between about 175 and 240 seconds, and carbon tetrachloride elution between about 250 and 363 seconds. The backflush valve 406 is actuated into its activated position at about 365 seconds into the cycle. The heavier halocarbons will elute between about 420 and 600 seconds. The backflush valve 406 is actuated back into its deactive position at 760 seconds ready to start the next cycle.

The bromine in chlorine analyzer 14, non-condensable gases in chlorine analyzer 16 and the halocarbons in chlorine analyzer 18 as described above in connection with FIGS. 2–3, FIGS. 4–8 and FIGS. 9–11, respectively, are adapted to receive the chlorine sample in gaseous form. As described above, if the sample is taken from the process stream at a point at which the chlorine is in liquid form, it is passed through the vaporizer 12 to convert it to a gaseous form before it passes to a respective analyzer.

It is possible, if desired, to modify slightly the respective analyzers 14, 16 and 18 so that the vaporizer 12 may be eliminated and the chlorine sample pass to the respective analyzer in its liquid form direct from the process stream.

Figure 2A:
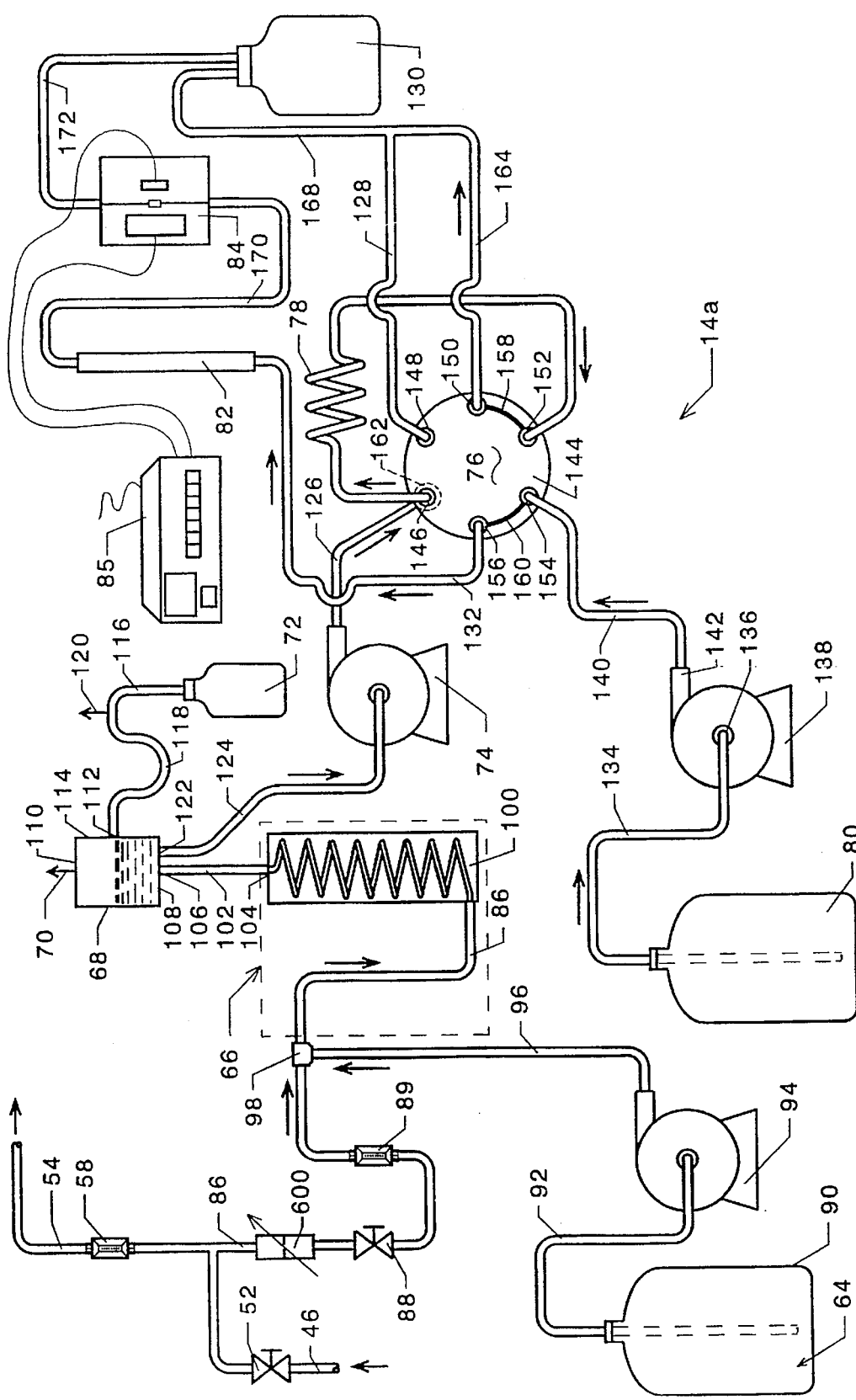
FIG. 2a is view similar to FIG. 2, but showing a modified analyzer for detecting and measuring bromine in chlorine.

An example of a modified form of a bromine in chlorine analyzer 14a which receives the chlorine in liquid form is shown in FIG. 2a. In this embodiment, the line 46, which in the modification of FIG. 2 is connected to the line 44 from the vaporizer 12, is instead connected to the line 30 coming directly from the process stream. Thus, the chlorine sample in the modification of FIG. 2a enters the analyzer through line 46 in liquid form.

The excess liquid chlorine exits the analyzer 14 through the sample return line 54 and is returned to the process stream. A portion of the chlorine from the line 52 is fed to the reaction zone 66 through the conduit 86. In this case, the conduit 86 is provided with an adjustable orifice 600 upstream of the valve 88. The orifice 600 serves to meter the liquid chlorine sample into the reaction zone with the chlorine sample in the line 46 upstream of the orifice 600 being maintained at a constant pressure against the orifice. A suitable metering pump may be used in place of the orifice.

With the embodiment of FIG. 2a, once the liquid chlorine is metered into the hydrazine in the reaction zone 66, the reaction and analytical cycle and the analyzer itself are the same as explained in connection with the embodiment of FIGS. 2 and 3. Accordingly, the same references numbers are used for the same elements.

Figure 4A:
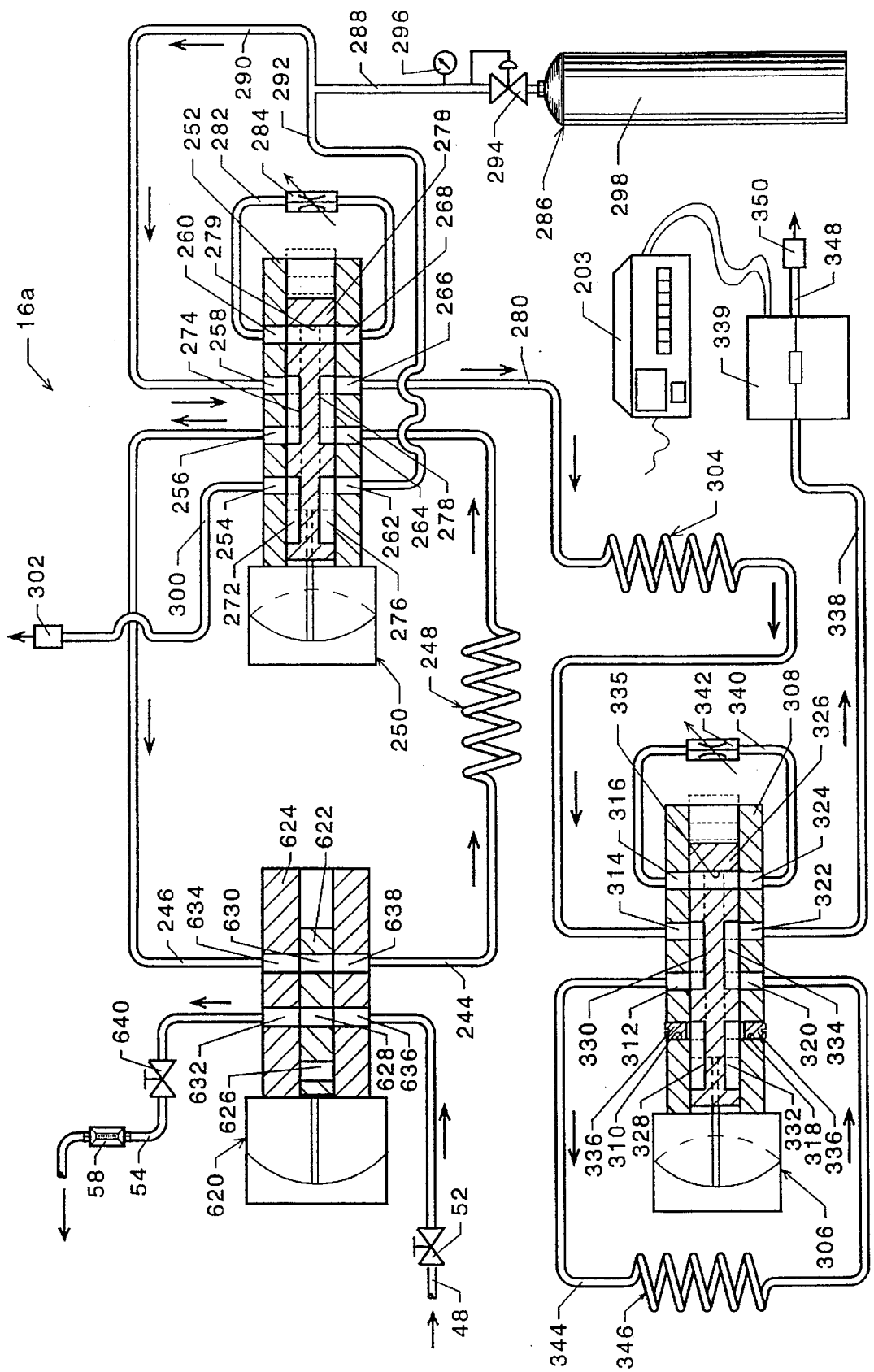
FIG. 4a is view similar to FIG. 4, but showing a modified analyzer for detecting and measuring non-condensable gases in chlorine.

FIG. 4a shows a modified non-condensable gas in chlorine analyzer 16a which may receive the chlorine sample in liquid form. In the case of this embodiment, the sample gathering and injection means of the embodiment of FIGS. 4–8, including the sample cut-off valve 202, the sampling valve 214, and the sample loop 238, is replaced by a sample injecting valve 620. Referring to FIG. 4a, the sample injecting valve 620 may be a standard, commercially available, pneumatically actuated, k-port sliding plate valve. The valve 620 is pneumatically actuatable between a deactive position and an activated, sample injecting position. A solenoid valve (not shown), controlled by the microprocessor 203, may control the supply of the pneumatic fluid such as instrument air to the valve 620 to cause the movement of the valve 620 between its two positions.

The sample injecting valve 620 may include a slider plate 622 movable in a body 624 between the two positions of the valve. The slider plate 622 may include three axially spaced through-bore or passages 626, 628 and 630, each of which extends between the top and bottom surfaces of the slider plate 622.

The body 624 of the sample injecting valve 620 may include four ports 632, 634, 636 and 638, with the ports 632 and 634 being positioned in the top surface of the body 624 and the ports 636 and 638 being positioned in the bottom surface of the body 624 when the valve is orientated as shown in FIG. 4a.

When the sample injecting valve 620 is in its deactive or loading position, the slider plate 622 is positioned as shown in FIG. 4a. In this deactive or loading position, the passage 628 connects the ports 632 and 636, while passage 630 connects the ports 634 and 638. Passage 626 is inactive.

When the valve 620 is actuated into its activated, or injecting position, the slider plate 624 is moved to the right as viewed in FIG. 4a. In this activated, or injecting position, the passage 626 connects the ports 632 and 636 and passageway 628 connects the ports 634 and 638. The passage 630 is inactive.

In the case of the modification of FIG. 4a, the line 48, which in the modification of FIGS. 4–8 is connected to the line 44 from the vaporizer 12, is instead connected to the line 30 coming directly from the process stream. Thus, the chlorine sample in the modification of FIG. 4a enters the analyzer through line 48 in liquid form. The line 48 is connected to the port 636 of the sample injecting valve 620. The sample return line 54 with the flow meter 58 therein is connected to the port 632 of the valve 620.

In the embodiment of FIG. 4a, the sample return line 54, at a point adjacent the valve 620, is provided with a needle valve 640 or other type of pressure control valve to maintain the pressure of the incoming liquid chlorine sample in the line 48 and as it passes through the valve 620 into the return line 54 to ensure that the chlorine sample passing through the valve 620 remains in liquid form.

The sample outlet line 244 containing the first chromatographic column 248 is connected to the port 638 and the carrier stream line 246 is connected to the port 634. The remainder of the analyzer 16a is as described in connection with the embodiment of FIGS. 4–8, with similar elements having like reference numerals.

In the deactive position of the analyzer 16a, the liquid chlorine sample from the process stream enters the analyzer through line 48 and enters the sample injecting valve 620 through the port 636, passes through passage 628, and exits the valve 620 through the port 632 into the return line 54. The first carrier gas stream flows through line 246 to the sample injecting valve 620, enters the port 634, passes through passage 630, and exits the valve 620 through the port 638 into line 244 and proceeds in a manner similar to its path in the FIGS. 4–8 embodiment.

When it is desired to take an analysis, the sample injecting valve 620 is caused to be moved into its activated position under the control of the microprocessor 203. In the activated position of the valve 620, the passage 628, containing a fixed volume slug of liquid chlorine sample, is moved into alignment with the ports 634 and 638 of the valve 620. In this position, the carrier fluid flowing into the valve 620 from line 246 through the port 634, carries the chlorine sample slug out of the sample injecting valve 620 through port 638 into line 244 to the chromatographic column 248. The carrier gas, being maintained at an elevated temperature, along with the reduction in pressure, causes the chlorine sample to vaporize into its gaseous form as its exits the valve 620. The analysis cycle then proceeds as described in connection with the embodiment of FIGS. 4–8.

Figure 9A:
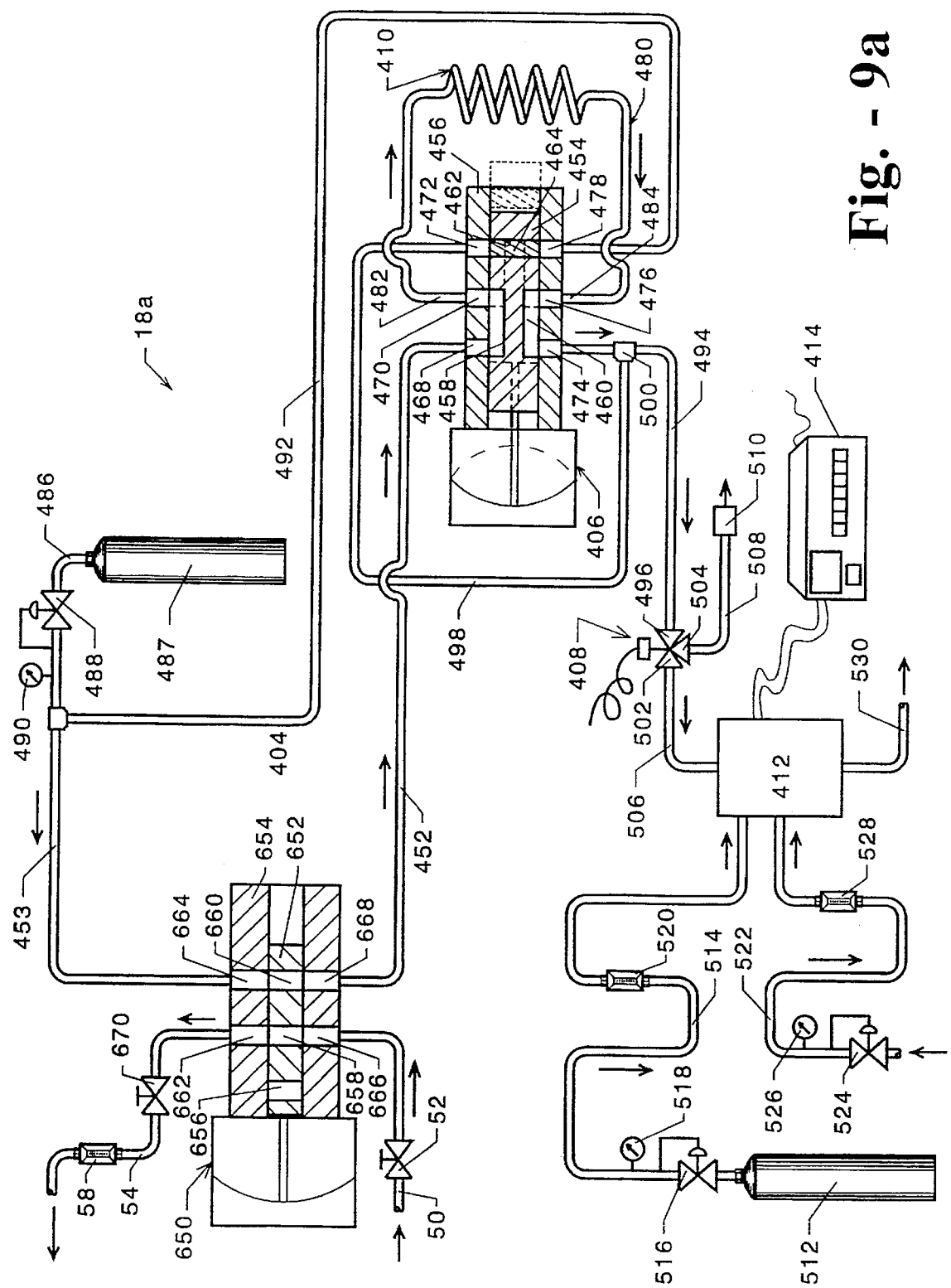
FIG. 9a is view similar to FIG. 9, but showing a modified analyzer for detecting and measuring halocarbons in chlorine.

In FIG. 9a there is shown a modified halocarbon in chlorine analyzer 18a which may receive the chlorine sample in liquid form. In the case of this embodiment, the sample gathering and injection means of the embodiment of FIGS. 9–11, including the sample cut-off valve 400, the sampling valve 402, and the sample loop 404, is replaced by a sample injecting valve 650.

Referring to FIG. 9a the sample injecting valve 650 is similar to the valve 620 shown and described in connection with FIG. 4a and may be a standard, commercially available, pneumatically actuated, 4-port sliding plate valve. The valve 650 is pneumatically actuatable between a deactive position and an activated, sample injecting position. A solenoid valve (not shown), controlled by the microprocessor 414, may control the supply of the pneumatic fluid such as instrument air to the valve 650 to cause the movement of the valve between its two positions.

The sample injecting valve 650 may include a slider plate 652 movable in a body 654 between the two positions of the valve. The slider plate 652 may include three axially spaced through-bore or passages 656, 658 and 660, each of which extends between the top and bottom surfaces of the slider plate 652.

The body 654 of the sample injecting valve 650 may include four ports 662, 664, 666 and 668, with the ports 662 and 664 being positioned in the top surface of the body 654 and the ports 666 and 668 being positioned in the bottom surface of the body 654 when the valve 650 is orientated as shown in FIG. 9a.

When the sample injecting valve 650 is in its deactive or loading position, the slider plate 652 is positioned as shown in FIG. 9a. In this deactive or loading position, the passage 658 connects the ports 662 and 666, while passage 660 connects the ports 664 and 668. Passage 656 is inactive.

When the sample injecting valve 650 is actuated into its activated, or injecting position, the slider plate 652 is moved to the right as viewed in FIG. 9a. In this activated, or injecting position, the passage 656 connects the ports 662 and 666 and the passageway 658 connects the ports 664 and 668. The passage 660 is inactive.

In the case of the modification of FIG. 9a, the line 50, which in the modification of FIGS. 9–11 is connected to the line 44 coming from the vaporizer 12, is instead connected to the line 30 coming directly from the process stream. Thus, the chlorine sample in the modification of FIG. 9a enters the analyzer through line 50 in liquid form. The line 50 is connected to port 666 of the sample injecting valve 650. The sample return line 54 with the flow meter 58 therein is connected to port 662 of the valve 650.

In the embodiment of FIG. 9a, the sample return line 54, at a point adjacent the valve 650, is provided with a needle valve 670 or other type of pressure control valve to maintain the pressure of the incoming liquid chlorine sample in the line 50 and as it passes through the valve 650 into the return line 54 to ensure that the sample passing through the valve remains in liquid form. The carrier-sample outlet line 452 is connected to the port 668 and the first carrier gas stream line 453 is connected to port 664. The remainder of the analyzer 18a is as described and shown in connection with the embodiment of FIGS. 9–11, with similar elements having like reference numerals.

In the deactive position of the analyzer 18a, the liquid chlorine sample from the process stream enters the analyzer through line 50 and enters the sample injecting valve 650 through the port 666, passes through the passage 658, and exits the valve 650 through the port 662 into the return line 54. The first carrier gas stream flows through line 453 to the sample injecting valve 650, enters the port 664, passes through the passage 660, and exits the valve 650 through the port 668 into the line 452 and proceeds in a manner similar to its path in the FIGS. 9–11 embodiment.

When it its desired to take an analysis, the sample injecting valve 650 is caused to be moved into its activated position under the control of the microprocessor 414. In the activated position of the valve 650, the passage 658, containing a fixed volume slug of liquid chlorine sample, is moved into alignment with the ports 664 and 668 of the valve 650. In this position of the valve 650, the carrier fluid flowing into the valve 650 from line 453 through port 664, carries the chlorine sample slug out of the passage 660 and through the port 668 of the sample injecting valve 650 into the line 452 to the backflush valve 406. The carrier gas, being maintained at an elevated temperature, along with the reduction in pressure, causes the chlorine sample to vaporize into its gaseous form as its exits the valve 650. The analysis cycle then proceeds as described in connection with the embodiment of FIGS. 9–11.

In the case of all the embodiments discussed above, all components, including the valves and piping, of each of the various analyzers, and the overall system, that are exposed to the virgin chlorine sample, or to a sample slug of chlorine being carried by the carrier gas which has a relatively high concentration of chlorine, should be fabricated from suitable chlorine resistant material. Such materials may include chlorine resistant plastics such as Teflon (polytetrafluoroethylene) and Kel-F® plastic (a chlorofluorohydrocarbon polymer) and metals such as nickel and other chlorine resistant metals.

By way of example, in the embodiment of FIGS. 2 and 3, all the components, including the lines 46, 54 and 86, valves 52 and 88, flow meters 58 and 89 and reactor 100, leading up to the separator 68 should be fabricated from chlorine resistant materials. In FIG. 2a, the orifice 600 should be of chlorine resistant material.

In the case of the embodiment of FIGS. 4–8, the sample cut-off valve 202 and sampling valve 214 are preferably fabricated from Kel-F® plastic while the lines 48, 54 and 212 and the tubular sample loop 238 are preferably fabricated from nickel. In the case of the embodiment of FIG. 4a, the sampling valve 620 is preferably fabricated from a chlorine resistant material such as Kel-F® plastic.

In the embodiment of FIGS. 9–11, the sample cut-off valve 400, the sampling valve 402, the backflush valve 406, and diverter valve 408 are preferably fabricated from a chlorine resistant plastic such as Kel-F® plastic, while the tubing forming the sample loop 404 and the chromatographic column 410 and the piping carrying the sample slug from the chromatographic column to the diverter valve as well as the piping exposed to the incoming chlorine sample from the process stream are preferably fabricated from nickel or Teflon. Such piping includes the lines 50, 54, 424, 452, 494 and 508. Any valve or flow meter within such lines should also be fabricated from chlorine resistant material. The sample injecting valves 620 and 650 of the embodiments of FIGS. 4a and 9a respectively, are also preferably fabricated from a chlorine resistant material such as Kel-F® plastic.

By virtue of the above described system and analyzers, there is provided an effective means for determining the product quality of chlorine. The system provides for the on-line detection and measurement of the significant contaminants which may be present in the chlorine including bromine, non-condensable gases and halocarbons. The various analyzers are capable of continuously detecting and measuring low concentrations of their respective contaminants with precision and accuracy, and the system provides a means for continuously providing information and data regarding the quality of the chlorine on a real time basis.

While the invention has been described above with reference to specific embodiments thereof, it is apparent that many changes, modifications and variations can be made without departing from the concept disclosed herein. Accordingly, it is intended to embrace all such changes, modifications and variations that fall within the spirit and broad scope of the appended claims.

What is claimed is:

1. A method of detecting the presence of bromine in a sample of chlorine comprising:
   a. reacting a bromine-containing gaseous stream of the chlorine sample with a liquid reagent to form an aqueous mixture containing bromide ions and chloride ions, and a gas,
   b. separating the gas from the aqueous mixture to provide a separated aqueous mixture containing the bromide ions and chloride ions,
   c. injecting a sample of the separated aqueous mixture containing the bromide ions and the chloride ions into a liquid carrier stream to form an aqueous mixture-containing carrier stream,
   d. separating said bromide ions from said chloride ions within said aqueous mixture-containing carrier stream to provide separated bromide and chloride ions in said carrier stream, and
   e. passing said carrier stream containing said separated bromide and chloride ions through an ultraviolet detector and detecting the presence of the bromide ion in the sample passing therethrough.

2. The method of claim 1 wherein the said stream of chlorine sample is in gaseous form.

3. The method of claim 2 wherein said stream of chlorine sample is taken from a chlorine stream in liquid form and further comprising the step of vaporizing said chlorine into its gaseous form prior to reacting said stream.

4. The method of claim 1 wherein said reacting of step (a) comprises reacting said chlorine sample with an aqueous solution of hydrazine to form chloride ions, bromide ions, and nitrogen gas, and said separating of step (d) comprises passing said carrier liquid with said injected sample through a chromatographic column to separate the chloride ions from the bromide ions.

5. The method of claim 4 wherein said carrier liquid is an aqueous solution of a chloride salt.

6. The method of claim 5 wherein said salt is selected from the group consisting of sodium chloride and potassium chloride.

7. The method of claim 1 wherein said stream of chlorine sample is taken from said chlorine stream in liquid form.

8. The method of claim 7 wherein said stream of chlorine is taken from a chlorine process stream in liquid form and further comprising the step of metering said liquid chlorine sample through an orifice into a reaction zone to react with said reagent.

9. The method of claim 7 wherein said chlorine is taken from a chlorine process stream in liquid form and further comprising the step of metering said chlorine by a metering pump into a reaction zone to react with said reagent.

\* \* \* \* \*